US011090387B2

(12) United States Patent
Burdick et al.

(10) Patent No.: US 11,090,387 B2
(45) Date of Patent: Aug. 17, 2021

(54) HYDROLYTICALLY DEGRADABLE POLYSACCHARIDE HYDROGELS

(75) Inventors: Jason Alan Burdick, Philadelphia, PA (US); Sujata Sahoo, Wilmington, DE (US); Cindy Chung, Palo Alto, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/139,537

(22) PCT Filed: Dec. 8, 2009

(86) PCT No.: PCT/US2009/067141
§ 371 (c)(1),
(2), (4) Date: Sep. 1, 2011

(87) PCT Pub. No.: WO2010/074958
PCT Pub. Date: Jul. 1, 2010

(65) Prior Publication Data
US 2012/0114615 A1 May 10, 2012

Related U.S. Application Data

(60) Provisional application No. 61/139,779, filed on Dec. 22, 2008.

(51) Int. Cl.
| A61K 35/12 | (2015.01) |
| A61K 47/36 | (2006.01) |
| A61K 38/19 | (2006.01) |
| C08B 37/08 | (2006.01) |
| C08B 37/00 | (2006.01) |
| A61K 47/34 | (2017.01) |
| A61L 27/58 | (2006.01) |
| A61L 27/52 | (2006.01) |
| A61L 27/18 | (2006.01) |
| A61L 27/38 | (2006.01) |
| A61L 27/54 | (2006.01) |
| C12N 5/0775 | (2010.01) |
| C12N 5/00 | (2006.01) |

(52) U.S. Cl.
CPC ............ *A61K 47/36* (2013.01); *A61L 27/18* (2013.01); *A61L 27/3834* (2013.01); *A61L 27/52* (2013.01); *A61L 27/54* (2013.01); *A61L 27/58* (2013.01); *C12N 5/0012* (2013.01); *C12N 5/0663* (2013.01); *A61L 2300/414* (2013.01); *A61L 2300/426* (2013.01); *A61L 2300/442* (2013.01); *A61L 2300/604* (2013.01); *A61L 2430/06* (2013.01); *C12N 2533/40* (2013.01); *C12N 2533/80* (2013.01)

(58) Field of Classification Search
USPC ............ 424/93.7; 514/772.7, 7.6, 777; 536/123.1, 53
See application file for complete search history.

(56) References Cited

U.S. PATENT DOCUMENTS

| 4,699,784 | A | 10/1987 | Shih et al. | |
| 5,834,029 | A * | 11/1998 | Bellamkonda et al. | ...... 424/570 |
| 7,220,270 | B2 * | 5/2007 | Sawhney et al. | ............. 606/193 |
| 2004/0028745 | A1 | 2/2004 | Bouhadir et al. | |
| 2004/0241241 | A1 | 12/2004 | Lopatin | |
| 2005/0271631 | A1 | 12/2005 | Lee et al. | |
| 2006/0173088 | A1 | 8/2006 | Nozaki et al. | |
| 2006/0229492 | A1 | 10/2006 | Gelfand et al. | |
| 2007/0059248 | A1 | 3/2007 | Unger et al. | |
| 2007/0122392 | A1 * | 5/2007 | Gerecht-Nir et al. | ..... 424/93.21 |
| 2007/0185008 | A1 * | 8/2007 | Hennink et al. | .................. 514/2 |
| 2007/0190018 | A1 | 8/2007 | Papisov | |
| 2007/0233219 | A1 | 10/2007 | Shafi et al. | |
| 2008/0065048 | A1 | 3/2008 | Sabbah et al. | |
| 2008/0279944 | A1 | 11/2008 | Sawhney | |
| 2009/0238875 | A1 | 9/2009 | Noh et al. | |
| 2010/0261196 | A1 | 10/2010 | Evans et al. | |

FOREIGN PATENT DOCUMENTS

WO  WO 2010/074958  7/2010

OTHER PUBLICATIONS

Myers, the Basics of Chemistry p. 74 2003.*
Csoka et al. (Genomics 60, 356-361 (1990) col. 1 p. 356) (Year: 1990).*
Bitter et al., "A Modified Uronic Acid Carbazole Reaction," Analytical Biochemistry, Oct. 1962, 4(4), 330-334.
Blom et al., "Infarct size reduction and attenuation of global left ventricular remodeling with the CorCap cardiac support device following acute myocardial infarction in sheep," Heart Fail Rev., Jun. 2005, 10(2), 125-139.
Burdick et al., "Controlled degradation and mechanical behavior of photopolymerized hyaluronic acid networks," Biomacromolecules, Jan.-Feb. 2005, 6(1), 386-391.
Christman et al., "Fibrin glue alone and skeletal myoblasts in a fibrin scaffold preserve cardiac function after myocardial infarction," Tissue Engineering, Mar.-Apr. 2004, 10(3-4), 403-409.
Christman et al., "Injectable fibrin scaffold improves cell transplant survival, reduces infarct expansion, and induces neovasculature formation in ischemic myocardium," Journal of the American College of Cardiology, Aug. 2004, 44(3), 654-660.
Dai et al., "Thickening of the infarcted wall by collagen injection improves left ventricular function in rats," Journal of the American College of Cardiology, Aug. 2005, 46(4), 714-719.
Davis et al., "Local myocardial insulin-like growth factor 1 (IGF-1) delivery with biotinylated peptide nanofibers improves cell therapy for myocardial infarction," Proceedings of the National Academy of Sciences of the United States of America, May 2006, 103(21), 8155-8160.
Dobner et al., "A Synthetic Non-degradable Polyethylene Glycol Hydrogel Retards Adverse Post-infarct Left Ventricular Remodeling," Journal of Cardiac Failure, Sep. 2009, 15(7), 629-636.
Eaton et al., "Regional Cardiac Dilatation after Acute Myocardial-Infarction—Recognition by 2-Dimensional Echocardiography," New England Journal of Medicine, Jan. 1979, 300(2), 57-62.

(Continued)

*Primary Examiner* — Anna R Falkowitz
(74) *Attorney, Agent, or Firm* — BakerHostetler

(57) ABSTRACT

Provided are polysaccharide compositions capable of controllable hydrolytic degradation and suitable for controlled release of therapeutic agents. Also provided are methods for synthesizing such compositions and a variety of applications in which the compositions may be used.

17 Claims, 28 Drawing Sheets

(56) References Cited

OTHER PUBLICATIONS

Enomoto et al., "Early ventricular restraint after myocardial infarction: Extent of the wrap determines the outcome of remodeling," Annals of Thoracic Surgery, Mar. 2005, 79(3), 881-887.

Epstein et al., "MR tagging early after myocardial infarction in mice demonstrates contractile dysfunction in adjacent and remote regions," Magnetic Resonance in Medicine, Aug. 2002, 48(2), 399-403.

Erlebacher et al., "Early Dilation of the Infarcted Segment in Acute Transmural Myocardial-Infarction—Role of Infarct Expansion in Acute Left-Ventricular Enlargement", Journal of the American College of Cardiology, Aug. 1984, 4(2), 201-208.

Fujimoto et al., "Synthesis, characterization and therapeutic efficacy of a biodegradable, thermoresponsive hydrogel designed for application in chronic infarcted myocardium," Biomaterials, Sep. 2009, 30(26), 4357-4368.

Gheorghiade et al., "Chronic heart failure in the United States: A manifestation of coronary artery disease," Circulation, Jan. 1998, 97(3), 282-289.

Gorman et al., "The potential role of ventricular compressive therapy," Surgical Clinics of North America, Feb. 2004, 84(1), 45-59.

Hochman et al., "Limitation of Myocardial Infarct Expansion by Reperfusion Independent of Myocardial Salvage," Circulation, Jan. 1987, 75(1), 299-306.

International Patent Application No. PCT/US2009/067141: International Search Report and Written Opinion dated Feb. 5, 2010, 12 pages.

Jackson et al., "Border zone geometry increases wall stress after myocardial infarction: contrast echocardiographic assessment," American Journal of Physiology—Heart and Circulatory Physiology. Feb. 2003, 284(2), H475-H479.

Jackson et al., "Extension of borderzone myocardium in postinfarction dilated cardiomyopathy," Journal of the American College of Cardiology, Sep. 2002, 40(6), 1160-1167.

Jneid et al., "Impact of time of presentation on the care and outcomes of acute myocardial infarction," Circulation, May 2008, 117(19), 2502-2509.

Kelley et al., "Restraining infarct expansion preserves left ventricular geometry and function after acute anteroapical infarction," Circulation, Jan. 1999, 99(1), 135-142.

Kloner et al., "New insights into the open artery hypothesis," Circulation Research, Jul. 2008, 103(1), 1-3.

Kofidis et al., "Novel injectable bioartificial tissue facilitates targeted, less invasive, large-scale tissue restoration on the beating heart after myocardial injury," Circulation, Aug. 2005, 112(9 Suppl.), I-173-I-177.

Kramer et al., "Regional Differences in Function within Noninfarcted Myocardium during Left-Ventricular Remodeling," Circulation, Sep. 1993, 88(3), 1279-1288.

Landa et al., "Effect of injectable alginate implant on cardiac remodeling and function after recent and old infarcts in rat," Circulation, Mar. 2008, 117(11), 1388-1396.

Leor et al., "A novel injectable alginate scaffold promotes angiogenesis and preserves left ventricular geometry and function after extensive myocardial infarction in rat," Circulation, Oct. 2004, Abstract #1334, 110(17) Suppl., III-279.

Leor et al., "Intracoronary Injection of In Situ Forming Alginate Hydrogel Reverses Left Ventricular Remodeling After Myocardial Infarction in Swine," Journal of the American College of Cardiology, Sep. 2009, 54(11), 1014-1023.

Lima et al., "Impaired Thickening of Nonischemic Myocardium during Acute Regional Ischemia in the Dog," Circulation, May 1985, 71(5), 1048-1059.

Mann D. L., "Mechanisms and models in heart failure: A combinatorial approach," Circulation, Aug. 1999, 100(9), 999-1008.

Markovitz et al., "Large Animal-Model of Left-Ventricular Aneurysm," Annals of Thoracic Surgery, Dec. 1989, 48(6), 838-845.

Miura et al., "Limitation of myocardial infarct size in the clinical setting: current status and challenges in translating animal experiments into clinical therapy," Basic Res. Cardiol., Nov. 2008, 103(6), 501-513.

Moainie et al., "Infarct restraint attenuates remodeling and reduces chronic ischemic mitral regurgitation after postero-lateral infarction," Annals of Thoracic Surgery, Aug. 2002, 74(2), 444-449.

Mukherjee et al., "Targeted myocardial microinjections of a biocomposite material reduces infarct expansion in pigs," Annals of Thoracic Surgery, Oct. 2008, 86(4), 1268-1276.

Opie L. H., "Ventricular Function. Essential Cardiology: Principles and Practice," ed. Rosendorff C., Humana Press, Totowa, 2nd Ed., 2005, pp. 37-54.

Pilla et al., "Early postinfarction ventricular restraint improves borderzone wall thickening dynamics during remodeling," Ann. Thorac. Surg., Dec. 2005, 80(6), 2257-2262.

Pilla et al., "Theoretic impact of infarct compliance on left ventricular function," Ann. Thorac. Surg., Mar. 2009, 87(3), 803-810.

Ryan, et al., "Dermal Filler Injection: A Novel Approach for Limiting Infarct Expansion," Annals of Thoracic Surgery, Jan. 2009, 87(1), 148-155.

Singelyn et al., "Naturally derived myocardial matrix as an injectable scaffold for cardiac tissue engineering," Biomaterials, Oct. 2009, 30(29), 5409-5416.

Wall et al., "Theoretical impact of the injection of material into the myocardium: A finite element model simulation," Circulation, Dec. 2006, 114(24), 2627-2635.

Weisman et al., "Myocardial Infarct Expansion, Infarct Extension, and Reinfarction-Pathophysiologic Concepts," Progress in Cardiovascular Diseases, Sep.-Oct. 1987, 30(2), 73-110.

Yu et al., "Restoration of left ventricular geometry and improvement of left ventricular function in a rodent model of chronic ischemic cardiomyopathy," Journal of Thoracic and Cardiovascular Surgery, Jan. 2009, 137(1), 180-187.

Ifkovits JL, "Injectable hydrogel properties influence infarct expansion and extent of postinfarction left ventricular remodeling in an ovine model", PNAS, 2010,107,25,11507-11512.

\* cited by examiner

NMR characterization of the synthesized MeLAHA macromer.
$^1$H NMR of the MeLAHA macromer with peaks matching labels of the final structure in Scheme 1 (A) and DOSY spectra of unmodified HA (B) and MeLAHA (C), indicating complete coupling.

NMR characterization of the synthesized MeLAHA macromer.
$^1$H NMR of the MeLAHA macromer with peaks matching labels
of the final structure in Scheme 1 (A) and DOSY spectra of unmodified
HA (B) and MeLAHA (C), indicating complete coupling.

NMR characterization of the synthesized MeLAHA macromer.
$^1$H NMR of the MeLAHA macromer with peaks matching labels of the final structure in Scheme 1 (A) and DOSY spectra of unmodified HA (B) and MeLAHA (C), indicating complete coupling.

Degradation of hydrogels formed from MeLAHA macromers. VEGF (A) and uronic acid (B) release from pure MeLAHA hydrogels (n ~ 3.0, modification ~ 10.5%) at various macromer concentrations[~1 (■), 2 (▲), and 4 (●) wt%]. Both values are plotted as the cumulative percent release measured using quantitative analyses.

Degradation of hydrogels formed from MeLAHA macromers. VEGF (A) and uronic acid (B) release from pure MeLAHA hydrogels (n ~ 3.0, modification ~ 10.5%) at various macromer concentrations[~1 (■), 2 (▲), and 4 (●) wt%]. Both values are plotted as the cumulative percent release measured using quantitative analyses.

MSC viability and interactions with copolymer HA hydrogels. Mitochondrial activity (MTT assay) after 7 days (A), Live/Dead after 6 and 72 h (B), and histology after 14 days (CS = chondroitin sulfate, H&E = hematoxylin and eosin) of MSCs encapsulated in copolymer HA hydrogels (MeHA/MeLAHA 100:0, 75:25, 50:50, 25:75; scale bar = 200 μm for Live/Dead and 100 μm for histology.

MSC viability and interactions with copolymer HA hydrogels. Mitochondrial activity (MTT assay) after 7 days (A), Live/Dead after 6 and 72 h (B), and histology after 14 days (CS = chondroitin sulfate, H&E = hematoxylin and eosin) of MSCs encapsulated in copolymer HA hydrogels (MeHA/MeLAHA 100:0, 75:25, 50:50, 25:75; scale bar = 200 μm for Live/Dead and 100 μm for histology.

MSC viability and interactions with copolymer HA hydrogels. Mitochondrial activity (MTT assay) after 7 days (A), Live/Dead after 6 and 72 h (B), and histology after 14 days (CS = chondroitin sulfate, H&E = hematoxylin and eosin) of MSCs encapsulated in copolymer HA hydrogels (MeHA/MeLAHA 100:0, 75:25, 50:50, 25:75; scale bar = 200 μm for histology.

HYDROLYTICALLY DEGRADABLE POLYSACCHARIDE HYDROGELS

CROSS-REFERENCE TO RELATED APPLICATIONS

This application is the National Stage of International Application No. PCT/US2009/067141 filed Dec. 8, 2009, which claims the benefit of U.S. Provisional Application No. 61/139,779, filed Dec. 22, 2008, the disclosures of which applications are incorporated herein by reference in their entireties for any and all purposes.

STATEMENT OF GOVERNMENT RIGHTS

This invention was made with government support under grant numbers DE015761 and DMR0520020 awarded by the National Institutes of Health. The government has certain rights in the invention.

TECHNICAL FIELD

The present invention relates to hydrolytically degradable polymer compositions and to the encapsulation of cells or controlled release of various agents from such compositions.

BACKGROUND

With advances in biotechnology has come an attendant interest in biocompatible compositions, such as hydrogels, that are useful alone, for the encapsulation of cells, or in controllably releasing therapeutic agents disposed within. Such gels are, in some cases, made up of polysaccharides, which are biological polymers that are found in numerous types of tissues and organisms and are capable of being crosslinked into hydrogels that encapsulate active agents (e.g., growth factors and other macromolecules) or cells for release or incubation by way of the hydrogel being degraded to liberate the encapsulated agent or cell.

These hydrogels, however, typically degrade only in the presence of enzymes that break down the polysaccharide backbone, and the hydrogels do not degrade solely based on exposure to an aqueous medium. Thus, such hydrogels are limited in that they are not useful in environments (such as the in vivo environment) that lack such enzymes but where degradation of the hydrogel is still needed to provide controlled release of an agent.

Accordingly, there is a need in the art for biocompatible compositions that degrade in the presence of an aqueous medium, e.g., water, so as to liberate an active agent disposed within the hydrogel. The value of such compositions would be further enhanced if the degradation rate of such compositions could be "tuned" or otherwise altered according to the needs of the user in order to provide the user some measure of control over the composition's degradation profile.

SUMMARY

In meeting the described challenges, the present invention first provides macromers, the macromers comprising a biocompatible backbone unit; a polymerizing moiety; and a hydrolytically degradable linker disposed between the biocompatible backbone unit and the polymerizing moiety.

Also provided are compositions, the compositions comprising a polymer comprising a plurality of repeat units, at least one repeat unit comprising a biocompatible backbone; and a hydrolytically degradable linker disposed between the biocompatible repeat unit and a crosslinker group, the crosslinker group binding the first repeat unit to a second repeat unit.

Further disclosed are methods of synthesizing a macromer, the methods comprising reacting a first compound comprising methacrylate with a compound comprising lactide to give rise to a second compound comprising a methacrylic group, a lactic acid, and an —OH end group; converting the —OH end group to a carboxylic acid end group; reacting the carboxylic acid end group to give rise to a functionalized end group; and reacting the functionalized end group with a salt of an acidic polysaccharide, so as to give rise to a macromer comprising a polymerizing moiety and a hydrolytically degradable linker.

Additionally provided are methods of controllably delivering an agent, the methods comprising disposing a quantity of an agent within a polymeric composition comprising a plurality of first repeat units, at least one first repeat unit comprising a biocompatible backbone; and a hydrolytically degradable linker bound to the biocompatible repeat unit, to the polymerizing moiety, or to both; exposing the delivery composition to an aqueous medium so as to hydrolyze the hydrolytically degradable linker such at least a portion of the quantity of the agent is released from the polymeric composition.

The claimed invention also provides methods of growing a cartilaginous tissue, the methods comprising providing a biocompatible scaffold polymeric material, the polymeric material being characterized as capable of effecting chondrogenesis in a stem cell; the polymeric material comprising a hydrolytically degradable linker; disposing a stem cell within the polymeric material; and modulating the environment surrounding the polymeric material such that the stem cell differentiates and gives rise to a cartilaginous material.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

(FIG. 9B) Degradation of acellular 5:0 (black) and 2:3 (white) MeHA wt %: MeCLHA wt % hydrogels;

DETAILED DESCRIPTION OF ILLUSTRATIVE EMBODIMENTS

Figure 1A:
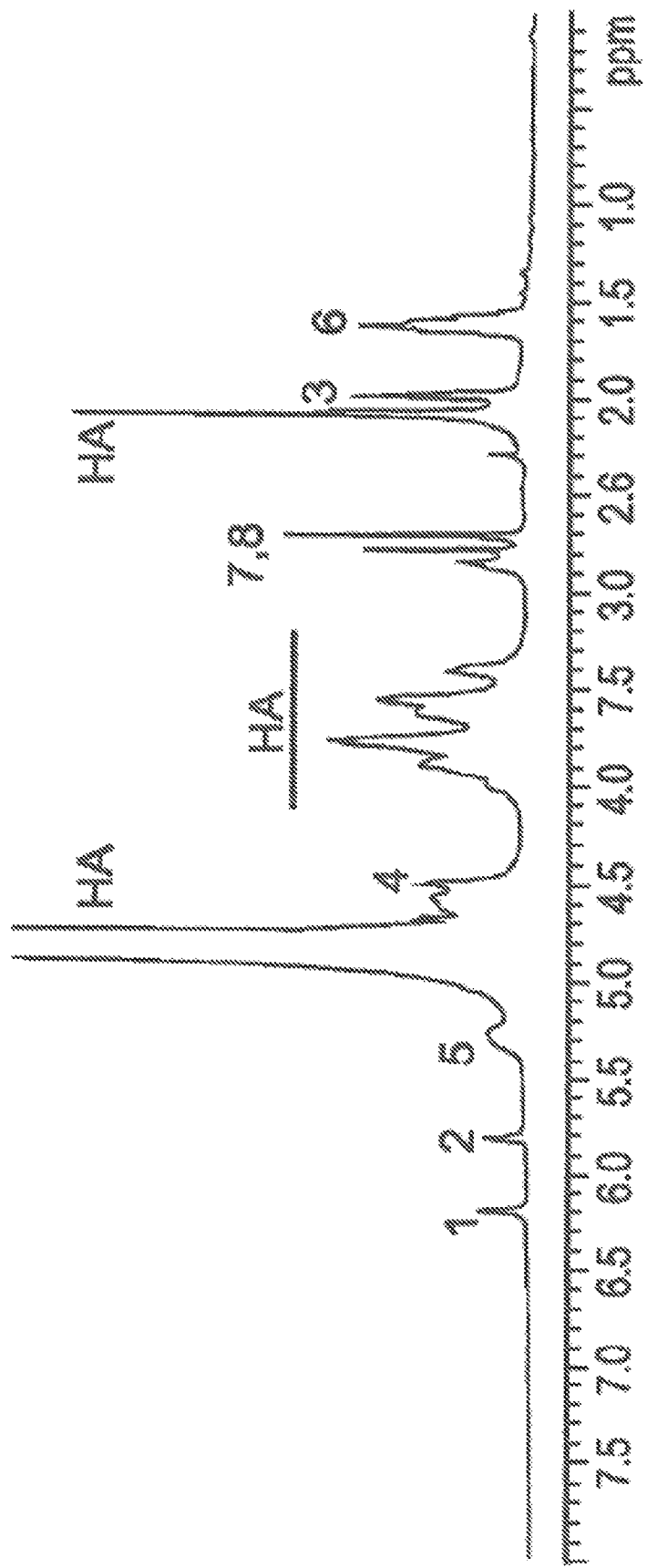
FIGS. 1A-1C depicts a NMR characterization of the synthesized methacrylate-lactic acid-hyaluronic acid (MeLAHA) macromer. 1H NMR of the MeLAHA macromer with peaks matching labels of the final structure in FIG. 16 (FIG. 1A) and DOSY spectra of unmodified HA (FIG. 1B) and MeLAHA (FIG. 1C), indicating complete coupling.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

Disclosed are macromers, said macromers including a biocompatible backbone unit; a polymerizing moiety; and a hydrolytically degradable linker disposed between the biocompatible backbone unit and the polymerizing moiety. Biocompatible backbone units suitably include polysaccharides, proteins, and the like.

A partial listing of polysaccharides that are useful in the claimed invention includes hyaluronic acid, amylase, amylopectin, glycogen, cellulose, heparin, agarose, alginate, and the like. Hyaluronic acid is considered or any combination thereof. In some embodiments—such as those embodiments that include hyaluronic acid—the biocompatible backbone unit is capable of enzymatic degradation.

In other embodiments, the biocompatible backbone is capable of hydrolytic degradation. Those embodiments are considered useful where a user may desire a degradable macromer whose degradation is dependent primarily on exposure to aqueous medium without the additional complication of a macromer that is also susceptible to enzymatic degradation. In some embodiments, the macromer is capable of both enzymatic and hydrolytic degradation.

The macromers may include a range of polymerizing moietes, such as acrylates, methacrylates, and the like. In some embodiments, the polymerizing moiety includes a carbon-carbon double or triple bond. The moiety is suitably polymerized by photopolymerization, by free radical-initiation, or by other methods of polymerization known to those of skill in the art.

Figure 1B:
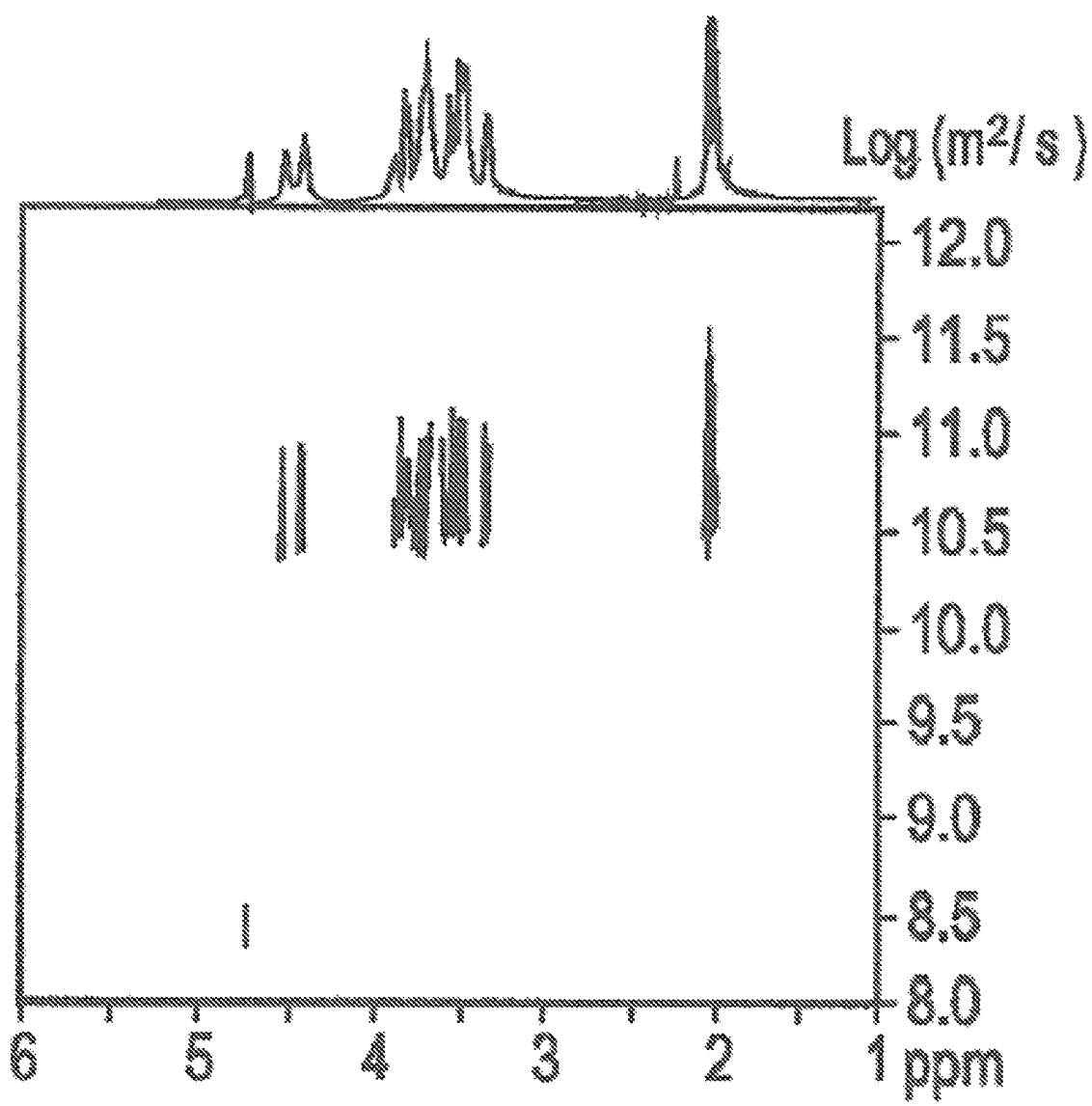
Figure 1C:
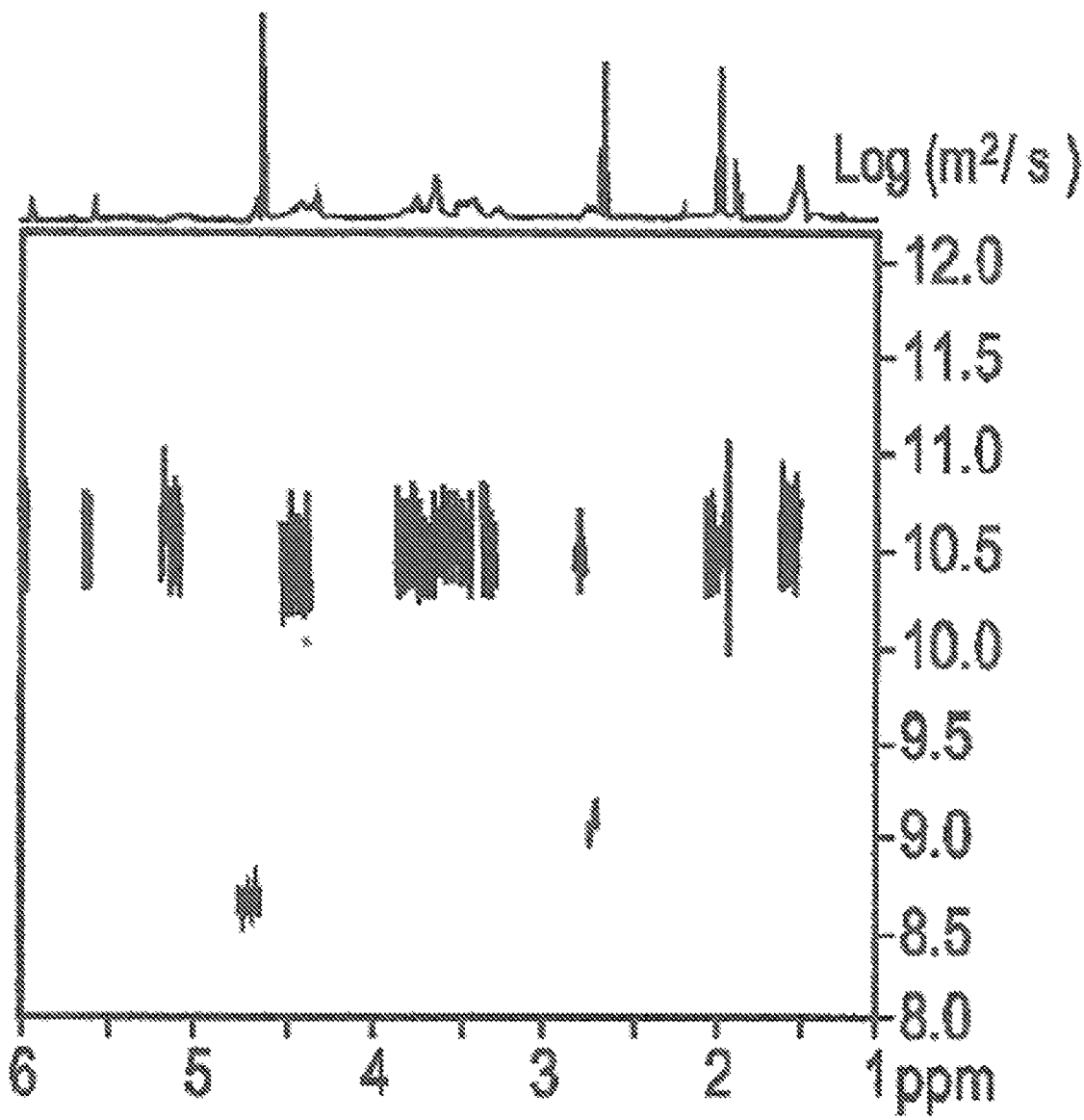
Figure 5:
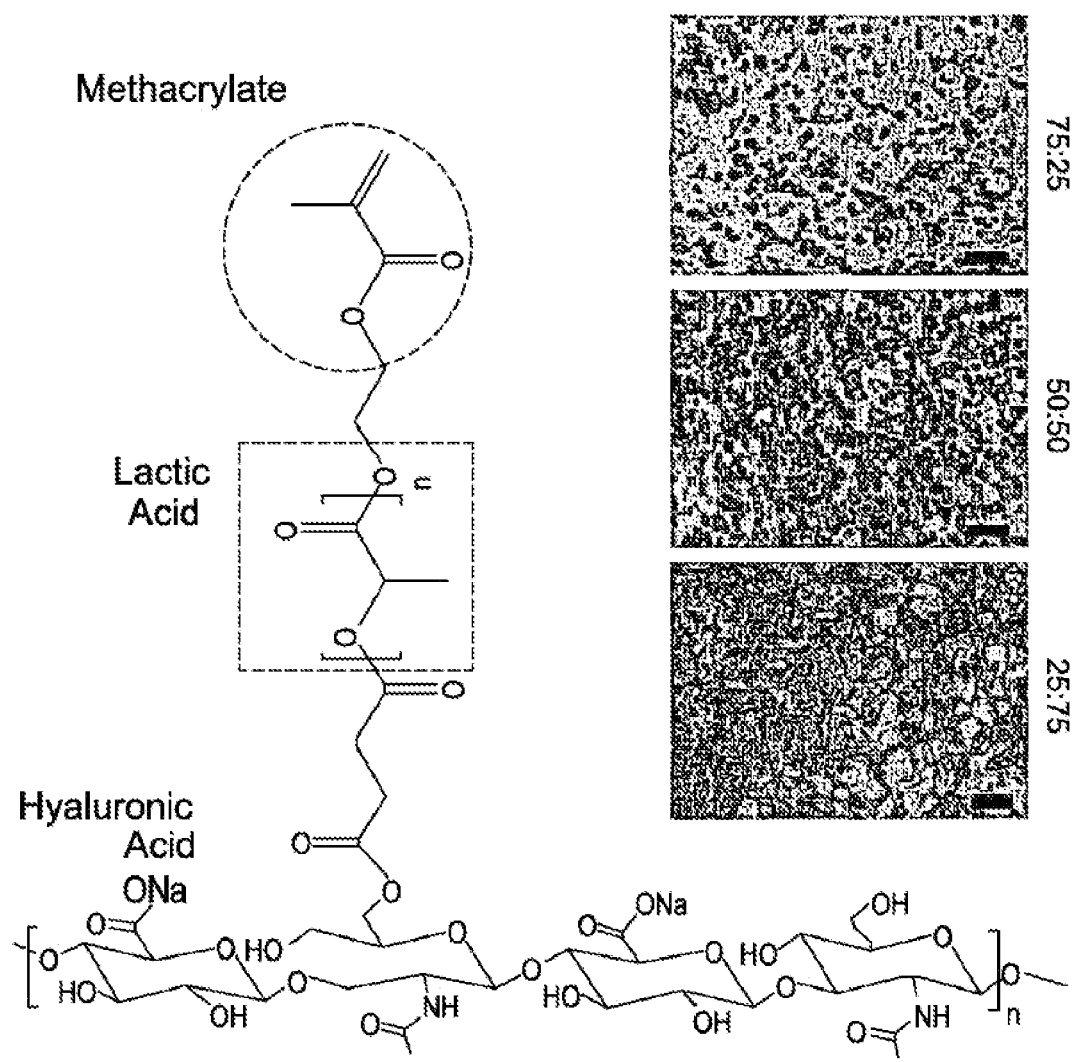
FIG. 5 depicts the chemical structure of synthesized hydrolytically degradable HA macromer (MeLAHA) incorporating reactive methacrylates and lactic acid units. The distribution of ECM molecules (CS shown) varies depending on the MeHA:MeLAHA ratio (scale bar=100 urn)
Figure 6:
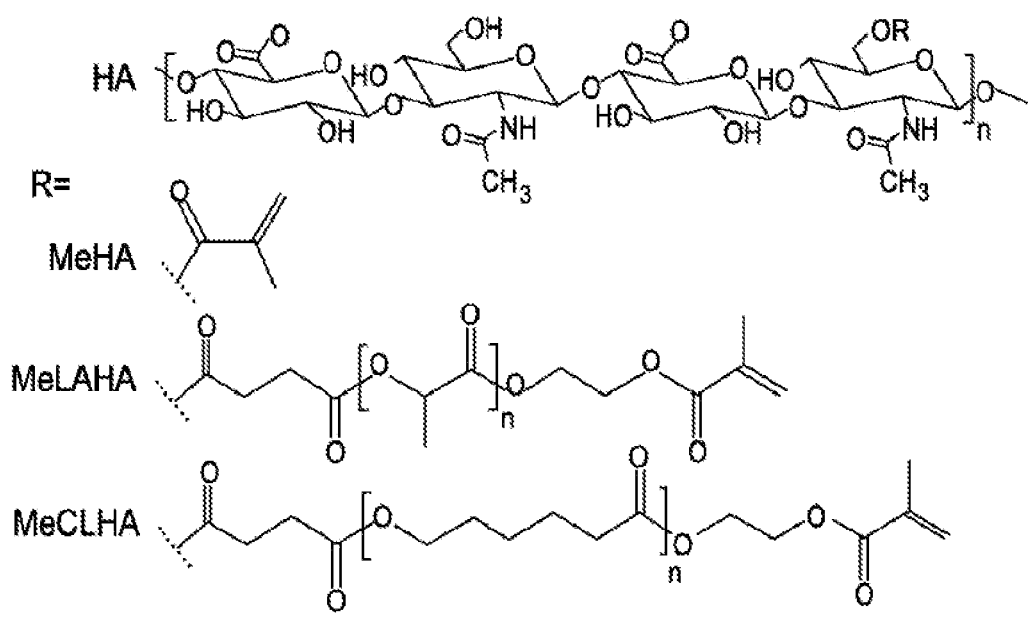
FIG. 6 depicts structures of HA macromers to be used with various side groups (MeHA, MeLAHA, MeCLHA) that lead to differential degradation.
Figure 16:
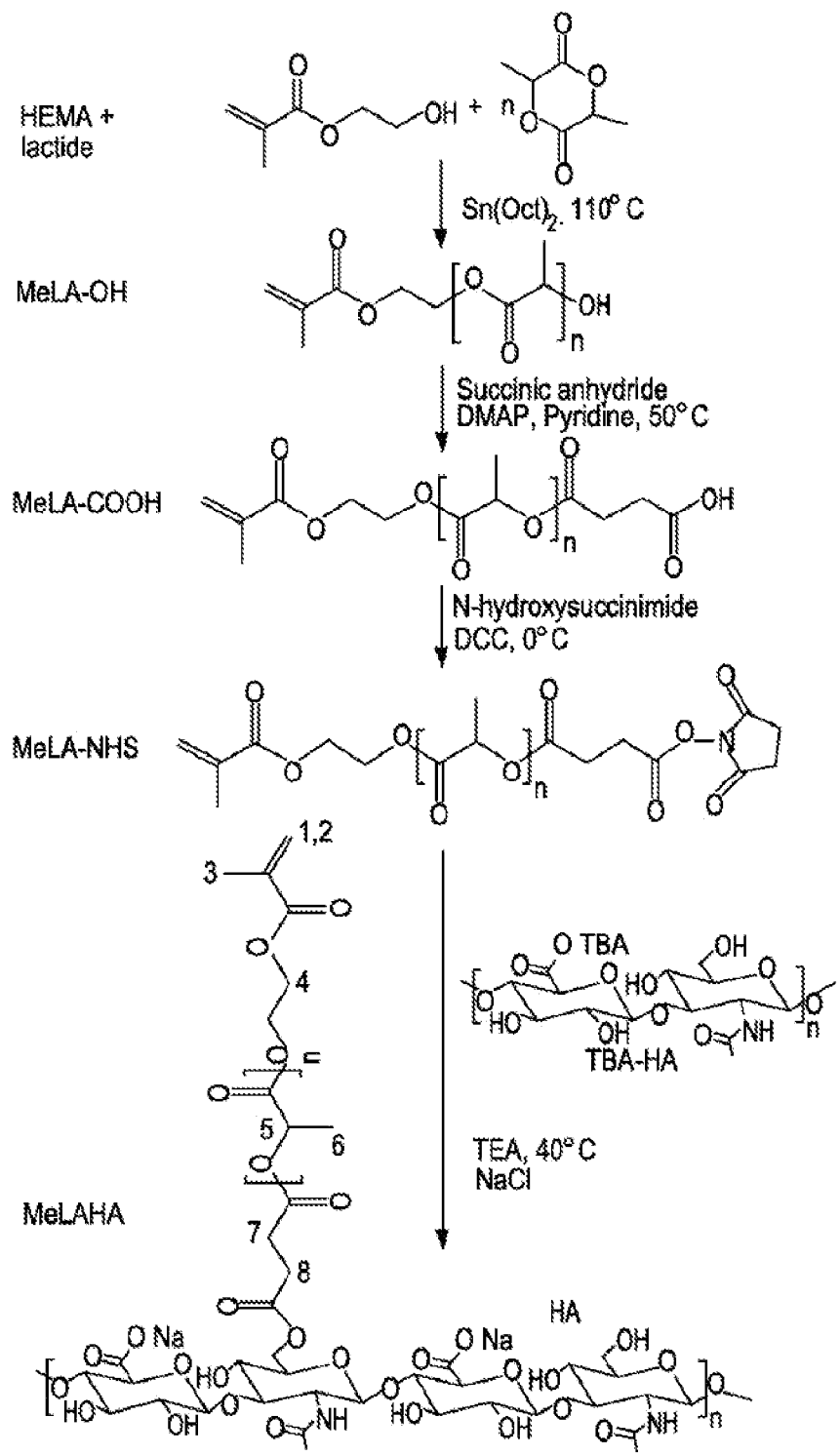
FIG. 16 depicts a sample approach to synthesizing the compositions of the claimed invention—in this scheme, HEMA=2-hydroxyethyl methacrylate, Me=methacrylate, LA=lactic acid, DMAP=dimethylaminopyridine, DCC=dicyclohexylcarbodiimide, NHS=N-hydroxysuccinimide, HA=hyaluronic acid, TEA=tetrabutylammonium, and TEA=triethylamine.

A variety of hydrolytically degradable linkers are useful in the present invention. Suitable linkers include a hydrolytically labile moiety, such as, for example, an ester. In some embodiments, the macromer includes more than one hydrolytically labile moiety; in others, the macromer includes a single hydrolytically labile moiety. A partial listing of linker groups includes, for example, glycolic acid, lactic acid, caprolactone, various anhydrides, and the like. Exemplary macromers are shown in FIG. 1, FIG. 5, and FIG. 16.

As non-limiting examples—discussed in more detail elsewhere herein—the composition may be a polymer of methacryl-lactic acid-hyaluronic acid, a polymer of methacryl-caprolactone-hyaluronic acid, and the like.

Figure 7:
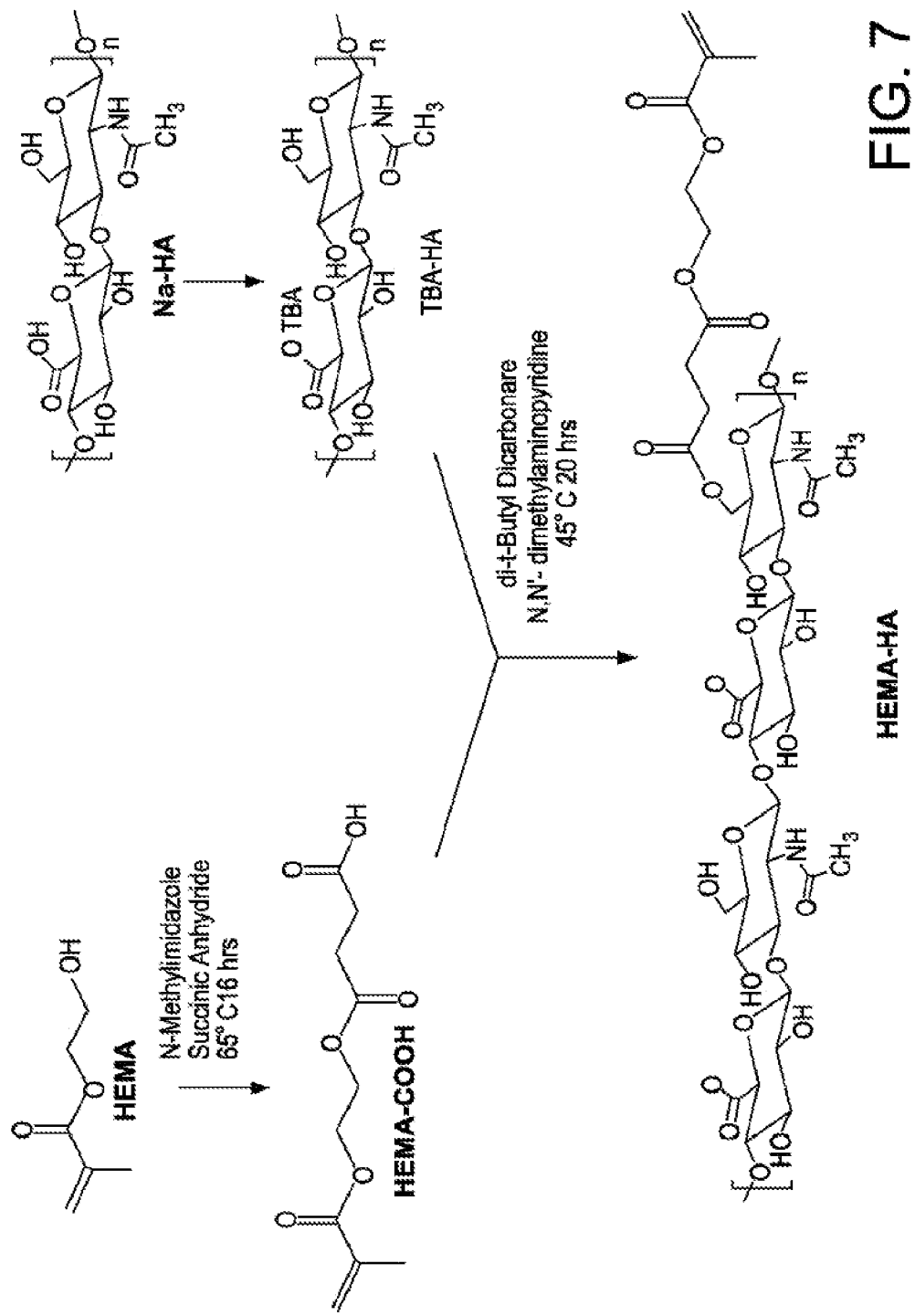
FIG. 7 depicts a sample, non-limiting synthesis scheme for compositions according to the claimed invention.

FIG. 7 also depicts a macromer according to the present invention. The macromer shown in that figure include a single ester group disposed between a polymerizable methacrylate group and the backbone. The hydrolytically degradable linker is suitably disposed between the backbone and the polymerizable linker.

Also disclosed are compositions, said compositions including a polymer comprising a plurality of repeat units. A repeat unit suitably a biocompatible backbone, a hydrolytically degradable linker disposed between the biocompatible repeat unit and a crosslinker group, the crosslinker group binding the first repeat unit to a second repeat unit.

The biocompatible backbone of the disclosed compositions suitably includes a biological molecule. Such molecules include polysaccharides, proteins, and the like, as described elsewhere herein. Hyaluronic acid is an especially suitable polysaccharide for certain applications that relate to production of cartilage and cartilaginous materials; other polysaccharides are also suitable for use in the claimed compositions. In some embodiments, the compositions may include a protein.

Hydrolytically degradable linkers are described elsewhere herein. Such linkers suitably include molecules that comprise an ester or other hydrolytically labile moiety. Lactic acid, caprolactone, glycolic acid, and the like are all considered suitable linkers.

In some embodiments, the polymer's repeat units are identical or substantially identical to one another. In other embodiments, the polymer includes two or more different repeat units. The polymer may include alternating repeat units, or, in other embodiments, may include a block of one kind of repeat unit that are adjacent to a block of another kind of repeat unit. Different repeat units may differ, for example, on the basis of their backbones, on their polymerizable groups, or on the basis of their hydrolytically degradable linkers, or on any combination of these.

The disclosed compositions can include an active agent, which agent can include a therapeutic agent, a marker, a label, a dye, and the like. Such active agents are suitably encapsulated within the composition so as to be controllably released from the composition as the composition degrades.

The disclosed compositions can also include a cell. The cells are suitably disposed or encapsulated within the compositions. Mammalian and stem cells—such as embryonic stem cells or mesenchymal stem cells (MSCs)—are considered especially suitable.

In one non-limiting embodiment, MSCs are encapsulated within a polymeric composition comprising hyaluronic acid. The compositions may include one or more components that are chosen based on their effect on a cell disposed within or otherwise in contact with the compositions. For example, hyaluronic acid may be chosen as part of a composition based on the hyaluronic acid's ability to interact with MSCs to dictate the way in which the MSCs differentiate.

Cells may be chosen based on their ability to produce a composition or material. For example, MSCs may be chosen based on their ability to differentiate into a form that produces cartilage-extracellular matrix material. It is contemplated that the various components of the disclosed compositions may be chosen or modified to as to induce a particular behavior or differentiation from a cell or other biological species or molecule disposed within or otherwise in contact with the composition.

In some embodiments, the compositions are characterized as being the polymerization products of the macromers described elsewhere herein. The compositions may also be copolymers, and in some embodiments, are copolymers of the macromers described elsewhere herein and one or more other molecules.

The compositions are suitably of a form that is characterized as a hydrogel; hydrogels typically possess properties that make them suitable for various biotechnology applications. The compositions, particularly when they are in hydrogel form, suitably include a plurality of crosslinks between two or more repeat units.

Hydrolytically degradable linkers suitable for use in the claimed compositions are described elsewhere herein. Such linkers suitably include an ester or other group that hydrolyzes in water or aqueous media.

Suitable crosslinker groups are also described elsewhere herein. Methacrylate groups are considered especially suitable, although other linkers previously described may be used, such as other linkers that include a carbon-carbon double bond.

In some embodiments the crosslinker groups connect one repeat unit to a separate repeat unit. In other embodiments, crosslinker groups on the same repeat unit interact with one another.

Also provided are methods of synthesizing macromers. These methods include reacting a first compound comprising methacrylate with a compound comprising lactide to give rise to a second compound comprising a methacrylic group, a lactic acid, and an —OH end group; converting the —OH end group to a carboxylic acid end group; reacting the carboxylic acid end group to give rise to a functionalized end group; and reacting the functionalized end group with a salt of an acidic polysaccharide, so as to give rise to a macromer comprising a polymerizing moiety and a hydrolytically degradable linker.

In some embodiments, the first compound comprises 2-hydroxyethylmethacrylate. Other methacrylates will be useful, and will be known to those of skill in the art.

Converting the —OH end group to a carboxylic acid group may, in some variations, entail reaction with succinic anhydride in the presence of pyridine and dimethylaminopropylpyridine. Reacting the carboxylic acid group, in some cases, entails reacting N-hydroxysuccinimide and dicyclyhexylcarbodiimide.

A variety of polysaccharide salts are useful in the claimed methods. For example, the salt of the acidic polysaccharide may comprise tetrabutyl amine.

The methods also suitably include the further step of polymerizing the macromer with at least one other macromer. Such polymerization may be accomplished by radical polymerization, by photopolymerization, or by other polymerization techniques known to those in the art.

Macromers may be polymerized with identical macromers. In some embodiments, a macromer is polymerized with another macromer or repeat unit that lacks a hydrolytically degradable linker.

Sample, non-limiting reaction methods are shown in FIG. 7 and FIG. 16. These schemes are also described in more detail in the Examples that follow.

Also disclosed are methods of controllably delivering an agent. These methods include disposing a quantity of an agent within a polymeric composition comprising a plurality of first repeat units, at least one first repeat unit comprising a biocompatible backbone; and a hydrolytically degradable linker bound to the biocompatible repeat unit, to the polymerizing moiety, or to both; exposing the delivery composition to an aqueous medium so as to hydrolyze the hydrolytically degradable linker such at least a portion of the quantity of the agent is released from the polymeric composition.

Suitable agents and polymeric compositions are described elsewhere herein. The hydrolysis can be accomplished in a controlled fashion, and the makeup of the polymeric composition may be tailored to achieve a particular release profile. For example, a composition may be formulated with linker groups that are known to be slow to hydrolyze in order to achieve a delayed release of the agent. In other embodiments, the composition may be formulated with linkers that hydrolyze at different rates so as to achieve a prolonged release of the agent over time. The relative proportions of linkers can be adjusted to achieve a range of release profiles, and the optimal proportion of linkers will be easily determined by those of skill in the art.

Exposing the composition to release the agent may be performed in vivo, i.e., inside a patient or subject. The composition may, of course, also be exposed to release an agent in a laboratory setting.

In some embodiments, the delivery composition is contacted to the tissue of a subject. Such tissue includes muscle tissue, vascular tissues, pulmonary tissue, or even neurological tissues. The delivery composition may be disposed there by polymerization in situ; i.e. by polymerizing the necessary monomer and other materials directly atop the tissue of interest. The delivery composition may also be synthesized apart from the tissue and then disposed atop the tissue.

To enhance the delivery of the agent from the delivery composition to the tissue, at least a portion of the delivery composition may be capped with a non-permeable or relatively high-density material so as to restrict release of the agent in the direction of the cap and direct release into the tissue. Such capping materials include, e.g., PEG hydrogels and other cross-linked materials. The capping material suitably has a crosslink density greater than the density of the delivery composition, as described elsewhere herein.

Suitable agents for delivery include, inter alia, stem cells, cytokines, chemotherapeutics, and the like. The release kinetics of the delivery agent can be controlled by modulating the degree of cross-linking in the delivery composition, as well as choosing agents based on their molecular weights.

Also provided are methods of growing a cartilaginous tissue. The methods include providing a biocompatible scaffold polymeric material, the polymeric material being characterized as capable of effecting chondrogenesis in a stem cell; the polymeric material comprising a hydrolytically degradable linker; disposing a stem cell within the polymeric material; and modulating the environment surrounding the polymeric material such that the stem cell differentiates and gives rise to a cartilaginous material.

Suitable polymeric materials are described elsewhere herein. MSC stem cells are considered suitable for these methods, particularly when the polymeric material comprises hyaluronic acid.

The environment surrounding the material may be modulated by exposing the material to an aqueous medium to promote the material's degradation. As described elsewhere herein, the material may be constructed such that the material degrades at a pre-determined rate. In some embodiments, the structure of the polymeric material is tailored to promote a particular morphology of the cell disposed within or in contact with the polymeric material.

EXAMPLES AND NON-LIMITING EMBODIMENTS

The following are sample embodiments of the claimed invention that are for illustrative purposes only and do not necessarily limit the scope of the claimed invention.

Example 1

Polysaccharides are suitable for being processed into biomaterials for numerous biological applications due to their native source in numerous tissues and biological functions. For instance, hyaluronic acid (HA) is found abundantly in the body, interacts with cells through surface receptors, and can regulate cellular behavior (e.g., proliferation, migration).

HA was previously modified with reactive groups to form hydrogels that are degraded by hyaluronidases, either added exogenously or produced by cells. These hydrogels, however, may be inhibitory and their applications are limited if the appropriate enzymes are not present. Synthesized here were HA macromers and hydrogels that are both hydrolytically (via ester group hydrolysis) and enzymatically degradable.

The hydrogel degradation and growth factor release was tailored through the hydrogel cross-linking density (i.e., macromer concentration) and copolymerization with purely enzymatically degradable macromers. When mesenchymal stem cells (MSCs) were encapsulated in the hydrogels, cellular organization and tissue distribution was influenced by the copolymer concentration. Importantly, the distribution of released extracellular matrix molecules (e.g., chondroitin sulfate) was improved with increasing amounts of the hydrolytically degradable component. The new macromer allowed for enhanced control over the structural evolution of the HA hydrogels toward applications as biomaterials.

HA is a linear polysaccharide of alternating o-glucuronic acid and N-acetyl-a-glucosamine, found natively in many tissues (e.g., cartilage), and degrades primarily by hyaluronidases found throughout the body or through oxidative mechanisms to yield oligosaccharides and glucuronic acid. HA plays a role in cellular processes like cell proliferation, morphogenesis, inflammation, and wound repair and interacts with cells through surface receptors (CD44, CD54, and CD168). These biological interactions make HA a candidate for the development of biomaterials that can directly interact with cells.

HA can be modified through its carboxyl and hydroxyl groups to form hydrogels in the presence of water. Such hydrogels are useful in tissue regeneration, drug delivery, and microdevices. As discussed, current hydrogels are limited in that (i) enzymes are needed to degrade the hydrogels, which can hinder the diffusion of growth factors, migration of cells, and distribution of extracellular matrix proteins if enzymes are not abundant, and (ii) degradation products are typically modified forms of HA (e.g., due to methacrylate addition) rather than potentially biologically active unmodified HA. Although an ester group may exist between the HA backbone and the reactive group, this bond is typically very stable, potentially due to steric hindrance or the hydrophobicity of the surrounding chemical groups.

Discussed below is one non-limiting method for synthesizing the disclosed novel HA macromer (MeLAHA), along with various applications related to release of growth factors and interactions with cells.

Experimental

Macromer Syntheses. A detailed description of the MeLAHA macromer synthesis is illustrated in FIG. 16. Briefly, 2-hydroxyethyl methacrylate (HEMA; 0.0549 mmol, Acros organics) is reacted with DL-lactide (0.0823 mmol, Polysciences) via a ring opening polymerization (110° C., 1 h, under nitrogen) in the presence of stannous octoate (0.0004 mmol, Sigma) to obtain MeLA-OH. The end group is converted into a carboxylic acid through reaction (50° C., 24 li, under nitrogen) of MeLA-OH (0.024 mmol) with succinic anhydride (0.024 mmol, Sigma) in the presence of pyridine (Sigma) and dimethylaininopyridine (DMAP; 0.002 mmol, Sigma) to obtain MeLA-COOH. The end group of the MeLA-COOH (0.008 mmol) is functionalized by reacting (0° C., 4 h and room temperature 24 h) with N-hydroxysuccinimide (NHS; 0.008 mmol, Sigma) and dicyclohexylcarbodihnide DCC; 0.008 mmol, Acros organics) to obtain MeLA-NHS. The sodium salt of HA (Lifecore, 64 kDa) is converted to a tetrabutylammonium (TBA; Sigma) salt by acidic ion exchange (room temperature, 8 h) with Dowex 50 W×8-200 resin, neutralized in aqueous TBA hydroxide for solubilization in anhydrous dimethyl sulfoxide (DMSO), coupled with MeLA-NHS (40° C., 24 h), and purified through precipitation in acetone to obtain MeLA-HA.

Each product was confirmed by $^1$H NMR (Bruker DMX 360 and 300 MHz spectrometer) and stored in acetone until use. Diffusion ordered NMR Spectroscopy (DOSY) spectra were recorded using stimulated echo Pulse sequence with bipolar gradients and a longitudinal eddy current delay in a Bruker DMX 600 MHz NMR spectrometer having z-gradient (maximum strength of 70 G/cm). The sine-shaped gradient pulse with 3.0 ms duration was logarithimically incremented in 32 steps, from 2% up to 95% of the maximum gradient strength. Diffusion time was set to 300 ms and a longitudinal eddy current delay of 5 ms was used. After Fourier transformation and baseline correction, DOSY spectra were processed using Bruker Topspin software's DOSY package.

MeHA was synthesized by the addition of methacrylic anhydride (~20-fold excess, Sigma) to a solution of 1 wt % HA (Lifecore, 64 kDa) in deionized water adjusted to a pH of 8 with 5 N NaOH and reacted on ice for 24 h. For purification, the macromer solution was dialyzed (MW cutoff 5-8 kDa) against deionized water for at least 48 h and the final product was obtained by lyophilization. $^1$H NMR was used to determine the final functionality and purity of the methacrylated HA (MeHA).

Hydrogel Formation. Hydrogels were synthesized by dissolving the MeLAHA or MeHA macromers at various concentrations (~1, 2, and 4 wt %) in phosphate buffered saline PBS). The photoinitiator, 2-methyl-144-hydroxyethoxy)phenyl-2-methyl-1-propanone (Irgacure 2959) was added at 0.05 .wt % and the macromer solution was placed into a mold (5 mm diameter, 2 mm thick) and polymerized with 2 mW/cm$^2$ ultraviolet light (~365 nm, IKO bulb) for 10 min. For growth factor release studies, human vascular endothelial growth factor (VEGF; R&D Systems) was added to the macromer solutions prior to photopolymerization.

Hydrogel Degradation and Growth Factor Release. After polymerization, the hydrogels (n=3 per composition) were placed in separate wells of a 24-well plate containing 1 mL of PBS and placed on an orbital shaker. The PBS containing the released VEGF and degradation products was removed at various time points and stored at ~20° C. The amount of uronic acid (a degradation component of HA) released during degradation was measured using a previously established carbazole reaction technique, and the VEGF concentration was determined in all of the samples using DuoSet ELISA development kits (R&D Systems) and reported as the fraction of the cumulative amount released with degradation.

Cellular Interactions with HA Hydrogels. Bone marrow-derived human MSCs (Lonza) were expanded in growth media (a-MEM, 16.7% PBS, 1% penicillin/streptomycin (PS), and 2 M L-glutamine) and encapsulated in the HA hydrogels at a density of 20×1.0 6 cells/mL. Constructs were cultured in chondrogenic media (DMEM-HG, 1.00 nM dexamethasone, 1% TS+ supplement, 1% PS, 40 ug/mL L-proline, 1 mM sodium pyruvate, 50,tig/mL ascorbic acid 2-phosphate, 10 ng/mL TGF-P3) at 37° C. and 5% CO, for up to 2 weeks. Cell viability was assessed visually using the Live/Dead cytotoxicity kit (Molecular Probes) or quantified using the MTT viability assay (ATCC). For histological analysis, constructs were fixed in 10% formalin for 24 h, embedded in paraffin, and processed using standard histological procedures. The histological sections (7 um thick) were stained with hematoxylin and eosin (H&E) to observe cell morphology and distributions within the hydrogel and immunohistochemistry for chondroitin sulfate using the Vectastain ABC kit (Vector Laboratories) and the DAB Substrate kit for peroxidase (Vector Laboratories). Sections were predigested in 0.5 ing/mL hyaluronidase for 30 min at 37° C. and incubated in 0.5N acetic acid for 4 h at 4° C. to swell the samples prior to overnight incubation with primary antibodies at a dilution of 1:100 (mouse monoclonal anti-chondroitin sulfate, Sigma).

Results and Discussion

Hydrolytically Degradable HA Macromer Synthesis. This approach involved the inclusion of hydrolytically degradable repeat units of alpha-hydroxy esters (e.g., lactic acid) between the HA and the polymerizing moiety (e.g., methacrylate). Since poly(lactic acid) is highly versatile in design, is hydrolyzable, and is approved by the FDA for several biomedical applications, it is a candidate for incorporation into the hydrogel. The general procedure for the macromer synthesis is outlined in FIG. 16.

First, lactic acid was polymerized off the hydroxyl terminal group of HEMA using a ring opening polymerization of lactide monomer in the bulk phase with stannous octoate (tin 2-ethylhexanoate) as a catalyst to form a hydroxyl terminated ethacrylated poly(lactic acid) (MeLA-OH). The polymerization proceeds through a coordination-insertion echanism and the number of lactic acid repeat units is readily controlled through the stoichiometric amount of lactide monomer to HEMA used in the reaction. The $^1$H NMR spectrum of this polymer displayed characteristic resonances for the methacrylate protons at δ 6.12 and 5.60 ppm and —CH and —CH3 protons of lactic acid at δ 5.19 and 1.52, ppm, respectively. From the integration ratio of the —CH proton corresponding to the lactic acid units to the methylene protons of the methacrylate group, the number of lactic acid repeat units was estimated (~3 for reported experiments).

Figure 2A:
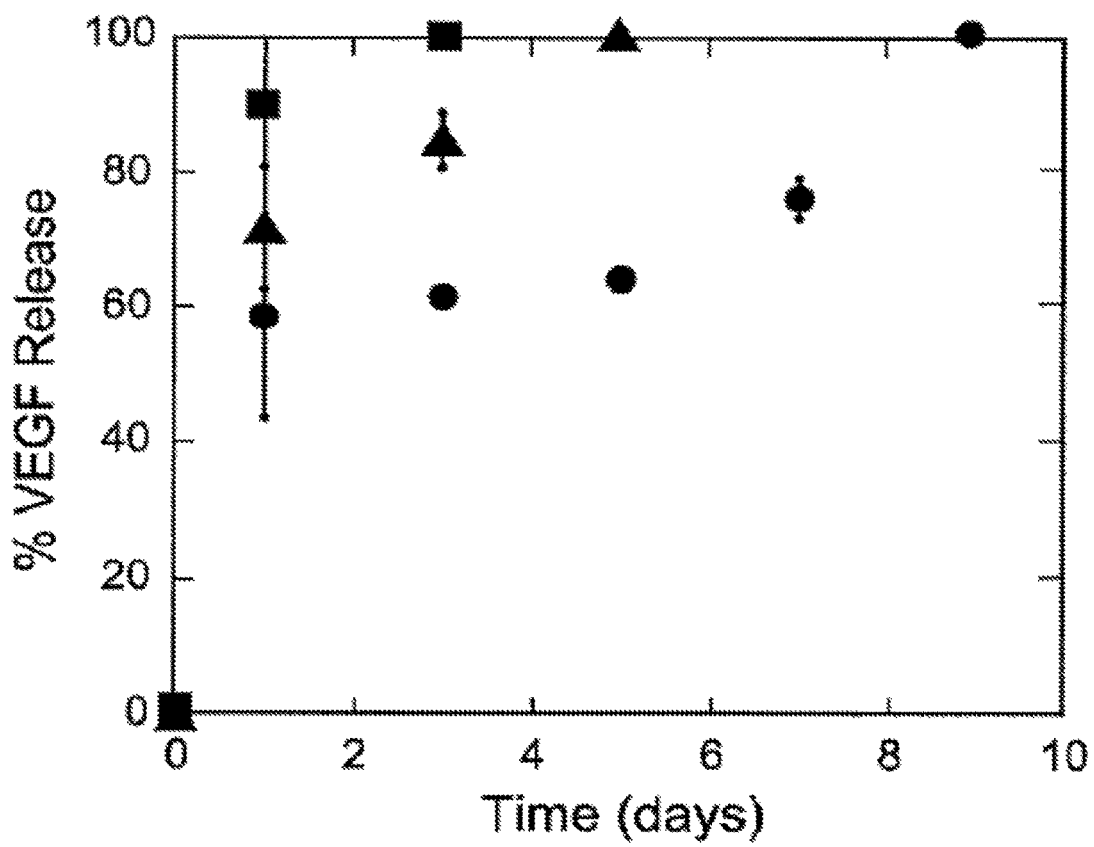
FIGS. 2A-2B depicts degradation of hydrogels formed from MeLAHA macromers. VEGF (FIG. 2A) and uronic acid (FIG. 2B) release from pure MeLAHA hydrogels (n~3.0, modification~10.5%) at various macromer concentrations [~1 (■), 2(▲), and 4 (●) wt %]—both values are plotted as the cumulative percent release measured using quantitative analyses.
Figure 2B:
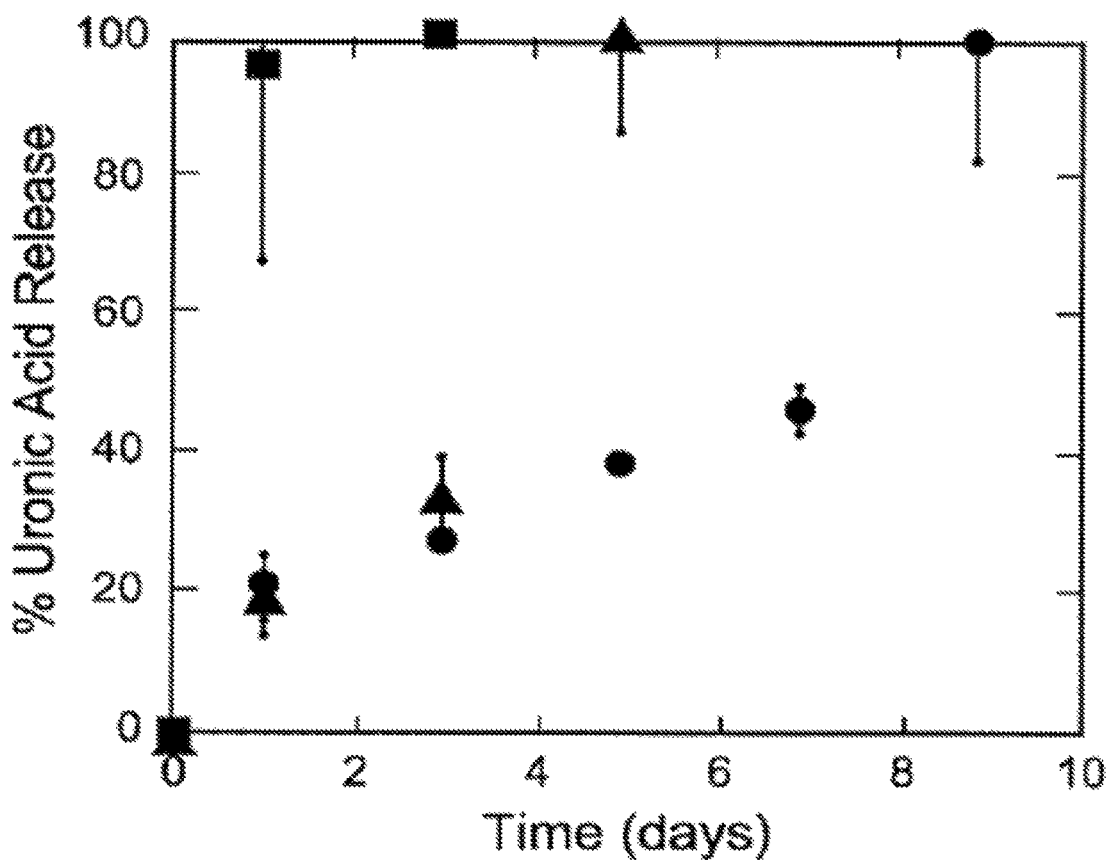

It was found that number of degradable units could be used to control the hydrolysis rate of hydrogels incorporating lactic acid. Without being bound to any particular theory, more repeat units led to more rapid degradation based on the greater probability of ester cleavage. Also, caprolactone could be substituted for lactide to incorporate a more slowly hydrolyzable group into the hydrogel. For coupling to HA, it was not possible to directly react the free hydroxyl group of MeLA-OH with HA because HA possesses both carboxylic acid and hydroxyl groups that would interfere with the reaction. Thus, the hydroxyl group of lactic acid was converted to a carboxylic acid through an esterification eaction with succipic anhydride in the presence of pyridine and dimethylaminopyridine (DMAP) as an esterification catalyst (FIG. 16) to form a carboxyl terminated methacrylated poly(lactic acid) (MeLA-COOH). The reaction was carried out in anhydrous tetrahydrofuran (TI-IF) because the acid anhydride is subjected to hydrolysis in aqueous medium. The conversion of —OH to —COOH was confirmed by $^1$H NMR (FIG. 2) with the δ 2.72 ppm resonance corresponding to the —$(CH_2)_2$ group of succinic anhydride observed in the spectrum.

Initial attempts to synthesize the acid chloride derivative of MeLA-COOH by reacting with thionyl chloride to couple to the carboxylic acid groups of HA were unsuccessful due to homopolymerization of the methacrylate groups. Thus, the N-hydroxysuccinimidyl ester derivative was formed for coupling to HA through reaction of MeLA-COOH with NHS in the presence of DCC (FIG. 16), where DCC promotes esterification by reacting with the end carboxyl group through nucleophilic substitution. The final product (MeLA-NHS) was obtained after filtering dicyclohexylurea (DCU) as the byproduct and 1H NMR confirmed successful modification.

Because the solubility of the sodium salt of HA is limited to aqueous solutions and the MeLA-NHS is not water-soluble, HA was converted to its TBA salt to make it soluble in highly polar organic solvents. After freeze-drying, HA-TBA was dissolved in DMSO and reacted with triethylamine (TEA) and MeLA-NHS for coupling (FIG. 16). The product was converted back to the sodium salt and precipitated in acetone to form MeLAHA. The derivatization reaction was confirmed by $^1$H NMR analysis (FIG. 1A) and exhibited distinct resonances from the —$CH_3$ protons of lactic acid at 1.58 ppm and the two protons of the methacrylate at δ 6.18 and 5.80 ppm. The degree of modification (~10.5%) was determined by the peak areas of the HA backbone and those of the methacrylate groups. DOSY was used to analyze the purified MeLAHA product (FIGS. 1B,C) to discriminate between different components of the sample by their chemical shift and diffusion behavior simultaneously. The separation in the diffusion dimension among various peaks is based on the self-diffusion coefficient of different species present in the solution. In a DOSY spectrum, molecules with lower molecular weights exhibit higher diffusion coefficients compared to polymers. However, if the same small molecule is attached to the polymer chain, the self-diffusion coefficient will be similar to the polymer. Comparing DOSY spectra in FIGS. 1B,C, it is clear that peaks due to MeLA (1.0-3.0 ppm and >5.0 ppm) show a similar diffusion coefficient to the HA peaks and confirms the coupling of MeLA to HA. In contrast, physical mixing of MeLA and HA shows significantly higher diffusion coefficient values for MeLA compared to HA. In addition, a slight reduction in the overall diffusion coefficient of MeLAHA was observed after coupling, indicating a higher molecular weight compared to unmodified HA.

Hydrolytically Degradable HA Hydrogel Characterization. With successful synthesis of the MeLAHA macromer, hydrogels were formed and characterized to illustrate the unique properties that are obtained with the new macromer design. The parameters that are readily controlled in this system include the molecular weight of the HA, the type (e.g., lactic acid versus caproic acid) and number (n) of hydrolytically degradable groups, the extent of coupling (percent of HA repeat units modified) of the degradable groups to the HA backbone, and the concentration of macromer used for hydrogel formation. In this study, one macromer (molecular weight~64 kDa, n~3.0, modification~10.5%) was synthesized and polymerized at various concentrations (~1, 2, and 4 wt %) using a photoinitiated polymerization with a growth factor (VEGF) present. These homopolymer hydrogels were placed in PBS, and the release of VEGF and a degradation product (uronic acid) was monitored with time.

The hydrogels completely degraded within 9 days without hyaluronidases present. A control hydrogel formed from MeHA without lactic acid units exhibited minimal degradation in this time period unless enzyme is added. Specifically, the MeHA hydrogels exhibit some uronic acid release within the first 24 h (~15-20%) and then no further release over the 9 day period. The initial release is attributed to potential sol fraction of the networks and incomplete polymerization at the polymer surface which is exposed to radical quenching oxygen species. These new hydrogels degrade into HA, lactic acid, and kinetic chains of poly(methacrylic acid). The release of VEGF and degradation products from the MeLAHA hydrogels (FIG. 2) was dependent on the macromer concentration during hydrogel formation, with faster degradation and growth factor delivery observed for more loosely crosslinked hydrogels (i.e., lower macromer concentrations).

A burst of VEGF release (>50%) was observed for all hydrogels, but the time for complete degradation and, consequently, VEGF release was dependent on the. Macromer concentration with the ~1, 2, and 4 wt % hydrogels degrading in ~3, 5, and 9 days, respectively. Without being bound to any one theory, this was perhaps dues to the fact that more time is needed for hydrolysis of the greater number of cross-links needed for complete degradation. One advantage to these hydrogel systems is that there was 100% encapsulation efficiency and release because the VEGF is directly incorporated into the hydrogel network during polymerization. VEGF was chosen for release due to the importance of HA on vascular differentiation. Due to the control that is obtained through not only macromer concentration, but other parameters (e.g., type of degradable units), a wide range of release profiles is possible.

Figure 3A:
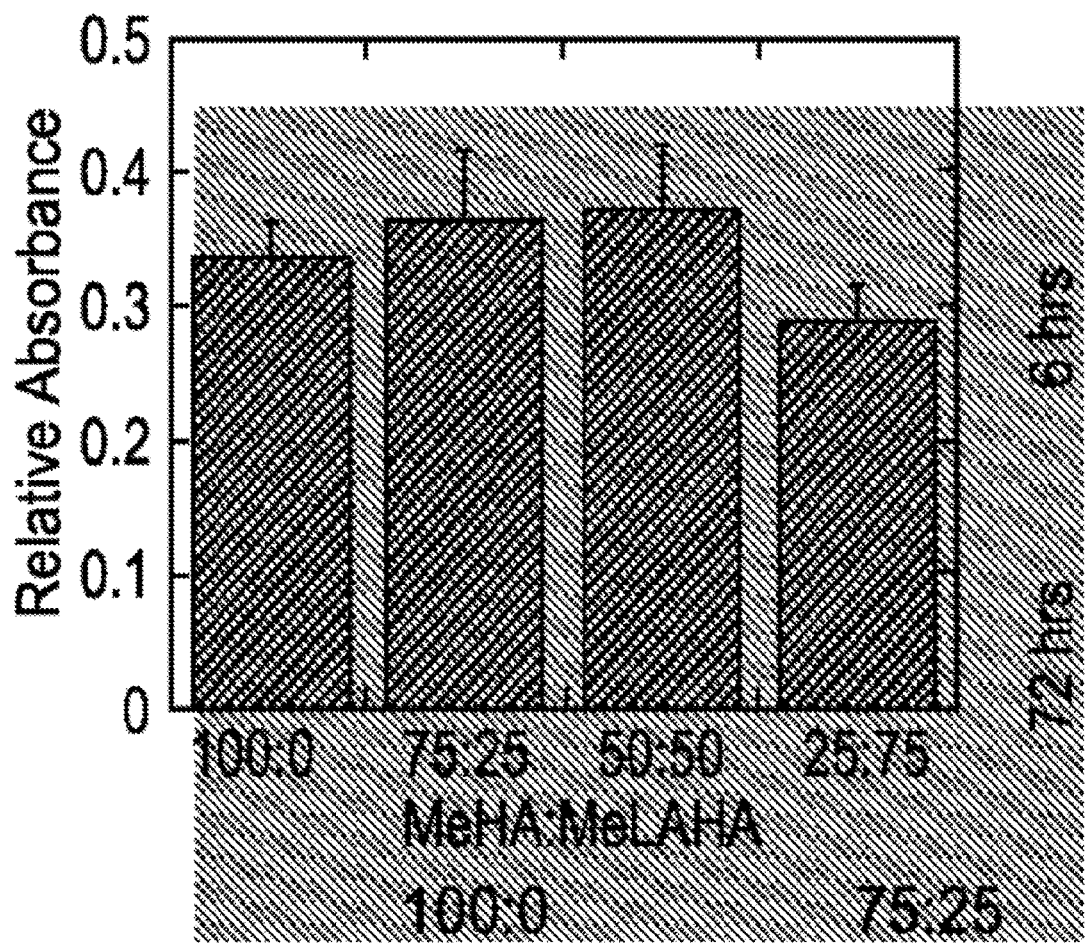
FIGS. 3A-3C depicts MSC viability and interactions with copolymer HA hydrogels. Mitochondrial activity (MTT assay) after 7 days (FIG. 3A), Live/Dead after 6 and 72 h (FIG. 3B), and histology (FIG. 3C) after 14 days (CS=chondroitin sulfate, H&E=hematoxylin and eosin) of MSCs encapsulated in copolymer HA hydrogels (MeHA/MeLAHA 100:0, 75:25, 50:50, 25:75; scale bar=200 um for Live/Dead and 100 um for histology), when the distribution of tissue produced by encapsulated MSCs was assessed, differences were also observed (FIG. 3C) after 2 weeks of culture in chondrogenic media.
Figure 3B:
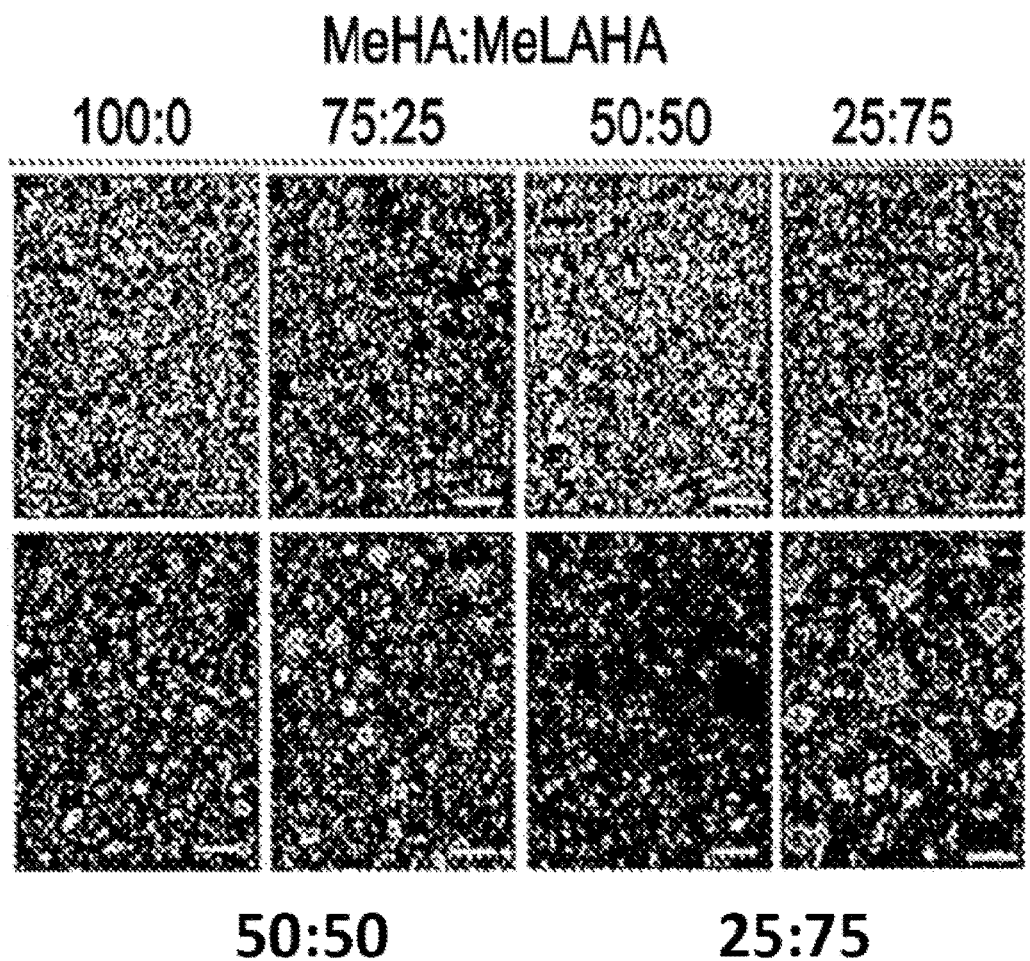

Cellular Interactions with Hydrolytically Degradable HA Hydrogels. For tissue engineering applications, the ability to entrap cells and to control cellular behaviors and tissue formation is essential. In this work, MSCs were chosen due to their ability to differentiate into various phenotypes and their clinical potential. Because the synthesized MeLAHA macromer degraded fairly quickly, it was copolymerized with MeHA (molecular weight~64 1:Da, modification~ 35%) at various ratios (100:0, 75:25, 50:50, 25:75, 0:100 MeHA/MeLAHA) and a concentration of ~2 wt % to obtain a wide range of networks exhibiting differential temporal structures. The MSCs remained viable (>95%) after encapsulation in all hydrogels, as evident by the mitochondrial activity after 7 days (FIG. 3A) and Live/Dead staining after 6 h and 3, days (FIG. 3B).

Figure 3C:
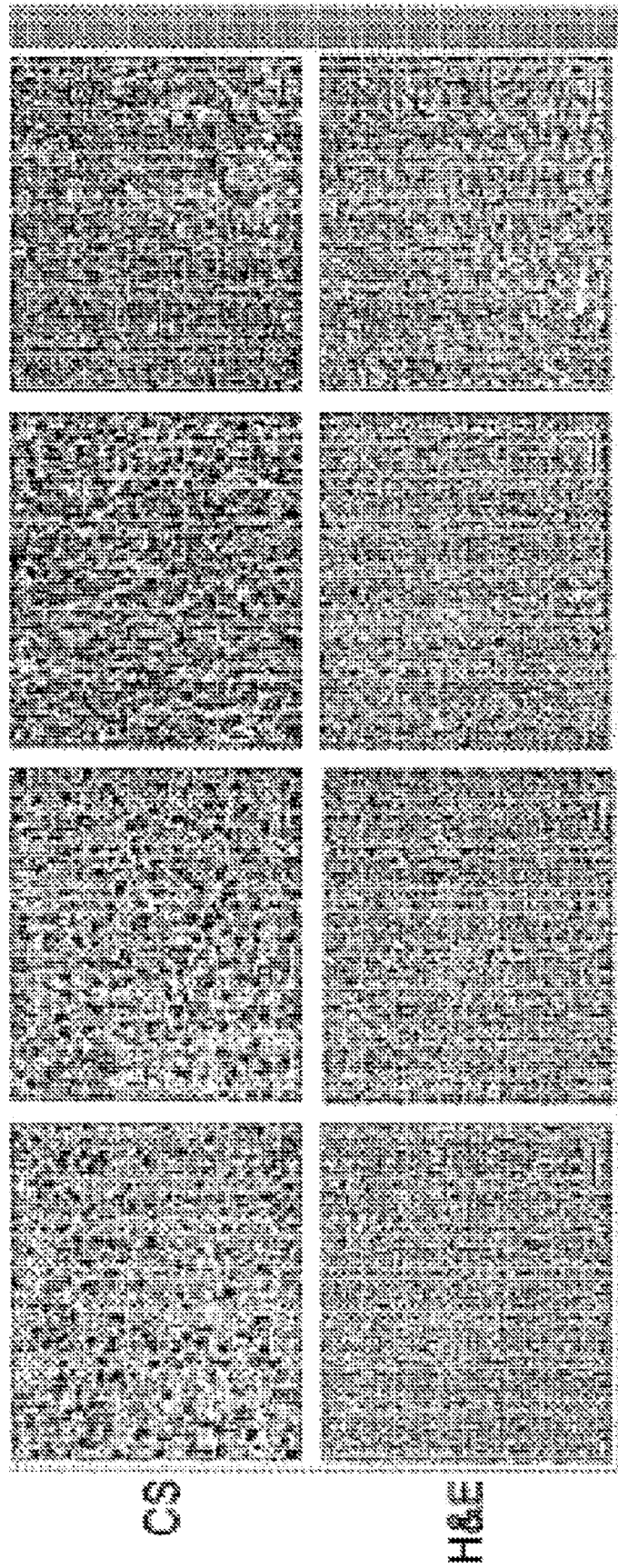

The 0:100 MeHA/MeLAHA degraded in less than 3 days and could not be analyzed further. The mitochondria] activity is similar between the groups after 7 days, but is slightly lower in the 25:75 MeHA/MeLAHA hydrogels, which may indicate differences in MSC proliferation. Importantly, the cells were homogenously viable in the constructs, yet the cellular morphology changed depending on the copolymer concentrations, with the greatest amount of hydrolytically degradable macromer leading to more cell clustering by the 3 day time point (FIG. 3B). When the distribution of tissue produced by encapsulated MSCs was assessed, differences were also observed (FIG. 3C) after 2 weeks of culture in chondrogenic media. In both chondroitin sulfate (CS) and hematoxylin and eosin (H&E) staining, greater molecule distribution and macroporosity were observed with increasing inclusion of the hydrolytically degradable macromer. Specifically, a gradient of CS (an important extracellular matrix molecule in cartilage) distribution corresponded with the amount of MeLAHA incorporated. Thus, more uniform tissues can be produced by altering degradation profiles with addition of the disclosed macromer.

HA hydrogels have been modified by others to manipulate degradation behavior. For instance, methacrylated HA has been copolymerized with a methacrylated version of aspartamide to form dynamic gels for drug delivery. However, this work involves the addition of a potentially toxic reagent to control the hydrogel properties, the synthesized hydrogels did not degrade completely in the absence of enzymes (incomplete susceptibility to hydrolysis), and no efforts were made to encapsulate cells in the hydrogels. Thus, the properties attained with this novel hydrogel presented here are advantageous for certain applications.

Although cartilage was used here as a model system, this approach has wide implications in the engineering of many tissues, specifically because degradation does not rely on potential issue-specific enzymes. Hydrogel chemistry and properties (e.g., mechanics and degradation) may play a role in the differentiation of stem cells. These parameters of the stem cell microenvironment must be controlled in the design of tissue engineering systems and may also be exploited for controlled differentiation, and thus it is important to have precise control over the material properties. This is possible with this reported material since degradation occurs via multiple mechanisms and can be altered to meet specific criteria.

SUMMARY

In summary, a non-limiting synthesis of a novel macromer that forms HA hydrogels that are hydrolytically degradable and have enhanced control over previously synthesized versions was explored. The synthetic scheme utilized several steps toward the coupling of a reactive methacrylate group polymerized with hydrolytically degradable repeat units to HA to form a macromer that can be photopolymerized into hydrogels for the encapsulation of growth factors or cells. Degradation of these hydrogels and subsequent growth factor release can be controlled by numerous factors, including the hydrogel cross-linking density. Finally, hydrogels and copolymer hydrogels (with purely enzymatically degradable HA macromers) supported the encapsulation of viable cells and the cellular morphology and the distribution of extracellular matrix molecules was dependent on the amount of hydrolytically degradable HA macromer. These results thus address the utility of engineering control over HA hydrogels in a variety of applications.

Example 2

Introduction

Photocrosslinkable polymers and specifically, hydrogels, are being developed for a variety of biomaterial applications ranging from tissue engineering scaffolds, drug delivery vehicles, and microfluidics components. The advantages to using photoinitiated polymerizations for these applications include the spatial and temporal control afforded to this type of radical polymerization and the uniform encapsulation of cells in 3D. These benefits have led to in vivo polymerizable materials, minimization of exotherms during polymerization, and the fabrication of scaffolds with patterned structures. Hyaluronic acid (HA) is found abundantly in the body and interacts with cells through surface receptors and can regulate cellular behavior (e.g., proliferation, migration). HA is modified with photoreactive groups using numerous procedures and can be used for the encapsulation of cells or for drug release.

The use of these hydrogels for the encapsulation of mesenchymal stem cells (MSCs) to control their differentiation was studied, as was control over hydrogel structure through the incorporation of hydrolytically degradable groups (e.g., lactic acid) or through copolymerizing with an alternate polysaccharide (e.g., chondroitin sulfate).

Experimental

HA Hydrogels and MSC Interactions. Methacrylated HA (MeHA) was synthesized through a reaction of HA (Lifecore, MW=64 kDa) with methacrylic anhydride. With the addition of a photoinitiator (0.05 wt % 12959), hydrogels were fabricated through a free radical photopolymerization with ultraviolet light (~1.8 mW/cm$^2$) exposure. Human MSCs (Lonza) were encapsulated in these and poly(ethylene glycol) (PEG 4600) hydrogels and cultured in growth and chondrogenic media. Constructs were analyzed for viability using Live/Dead staining, for gene expression (Type I and II collagens, aggrecan, Sox-9), and immunostained for Type I and Type II collagens and chondroitin sulfate (CS).

Hydrolytically Degradable HA Hydrogels. A detailed description of the MeLAHA macromer synthesis can be found elsewhere. Briefly, hydroxy ethyl methacrylate (HEMA) is reacted with DL-lactide via a ring opening polymerization in the presence of stannous octoate. The end group is converted into a carboxylic acid through reaction with succinic anhydride in the presence of pyridine and dimethylaminopyridine and subsequently functionalized by reacting with N-hydroxysuccinimide (NHS) and dicyclohexylcarbodihnide. The sodium salt of HA (Lifecore, 64 kDa) is converted to a tetrabutylammonium (TBA) salt by acidic ion exchange with Dowex 50 W×8-200 resin, neutralized in aqueous TBA hydroxide for solubilization in DMSO, coupled with MeLA-NHS, and purified through precipitation in acetone to obtain MeLAHA. Each product was confirmed by NIVIR and stored in acetone until use. DOSY spectrum were recorded using stimulated echo pulse sequence using bipolar gradients with a longitudinal eddy current delay in Bruker DMX 600 MHz NMR spectrometer having z-gradient (maximum strength of 70 G/cm). MSCs were encapsulated in the hydrogels and copolymers of MeHA and MeLAHA as described above and the viability and tissue distribution were assessed after culture in chondrogenic media in vitro.

Results and Discussion

Figure 4:
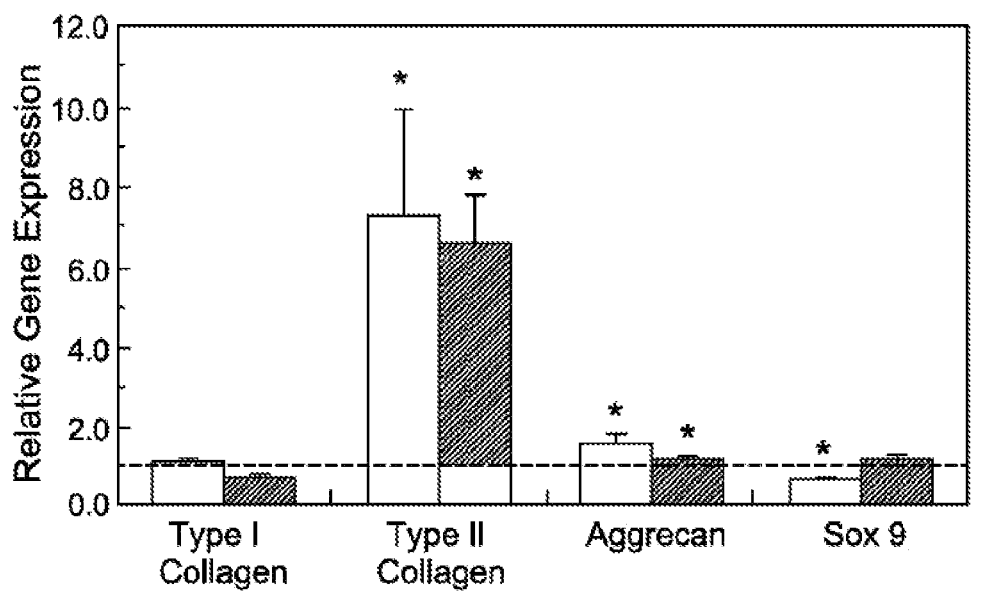
FIG. 4 depicts gene expression (top) for MSCs encapsulated in HA hydrogels normalized to MSCs in PEG hydrogels after 7 (white) and 14 (black) days in vitro and immunohistochemistry (bottom) of these hydrogels was performed after 14 days of in vitro culture (scale bar=100 um, *p<0.05)
Figure 4:
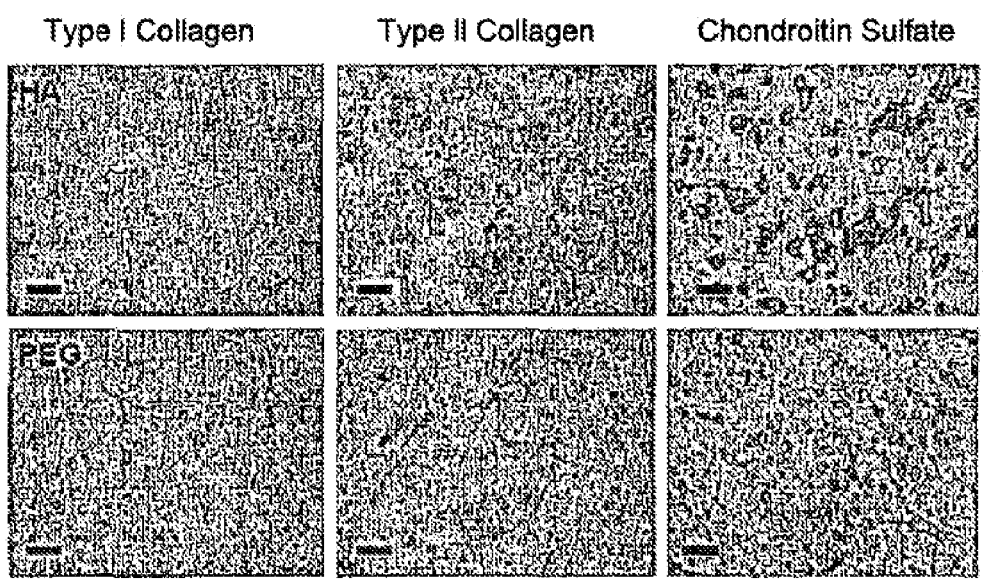

Hyaluronic Acid Hydrogels. To overcome issues with cell source in cartilage tissue regeneration applications, MSCs have generated significant interest as an alternative to autologous chondrocytes. Since MSCs have surface receptors (CD44) for HA, MeHA hydrogels may provide a stimulatory and cell-instructive environment for MSCs. Furthermore, MSCs have been successfully encapsulated in MeHA hydrogels with good cell viability and are capable of undergoing chondrogenic differentiation with the addition of TGF-133 in vitro (results not shown). When compared to culture in relatively inert PEG hydrogels (FIG. 4), an increase in the expression of chondrogenic markers (i.e., Type 11 collagen, aggrecan, sox-9) and enhanced staining of extracellular matrix molecules (e.g., chondroitin sulfate) were observed for MSCs. In these studies, both the viability and hydrogel mechanics were maintained between hydrogel types. Additionally, MSCs expressed multiple isoforms of hyaluronidases in standard cultures and in these hydrogels, and thus, can potentially remodel the matrix (results not shown). In vivo, with the incorporation of growth factors, the hydrogel influence on differentiation was diminished. This study provided evidence that the hydrogel chemistry plays a role in the chondrogenic differentiation of MSCs, potentially through receptor interactions.

Hydrolytically Degradable Hydrogels. As discussed, HA can be modified with reactive groups to form hydrogels that are degraded by hyaluronidases either added exogenously or produced by cells. However, these hydrogels may be inhibitory (e.g., to matrix distribution) and their applications limited if the appropriate enzymes are not present. In this example, synthesized HA macromers (MeLAHA, FIG. 5) and hydrogels were synthesized that are both hydrolytically (via ester group hydrolysis) and enzymatically degradable. The hydrogel degradation and growth factor release was tailored through the hydrogel crosslinking density (i.e., macromer concentration) and copolymerization with purely enzymatically degradable macromers. When MSCs were encapsulated in the hydrogels, cellular organization and tissue distribution was influenced by the copolymer concentration. The distribution of released extracellular matrix molecules (e.g., chondroitin sulfate, FIG. 5) was improved with increasing amounts of the hydrolytically degradable component. These structural changes did not lead to changes in overall cellular viability, but did influence cell organization with more clustering as the amount of hydrolytically degradable component increased. Although not shown here, the release of growth factors (e.g., vascular endothelial growth factor) was also controlled by the degradation of the hydrogels (results not shown). The disclosed macromers allowed for enhanced control over the structural evolution of the HA hydrogels towards applications as biomaterials.

SUMMARY

Polysaccharides have wide applicability as biomaterials and can be processed into a range of structures from hydrogels to microspheres. When MSCs are encapsulated into HA hydrogels, there are potential receptor interactions that occur and dictate the differentiation of the cells. When compared to inert gels, MSC chondrogenesis was upregulated in HA hydrogels. To better control the temporal behavior of HA hydro-gels, even without enzymes present, a degradable lactic acid unit was included between the HA backbone and reactive moiety. This led to hydrolysis and hydrogel degradation, which could be used to control matrix distribution by entrapped cells or the release of growth factors. The degradation rate could also be tuned by the macromer concentration. Finally, copolymerization with alternate polysaccharides was possible and degradation could be altered, but was dependent on the type of enzyme present. Towards future work with these materials, microspheres could also be formulated by the various macromers. These these results indicate the better understanding of polysaccharide materials towards their processing and use in the biomaterials.

Example 3

Figure 11A:
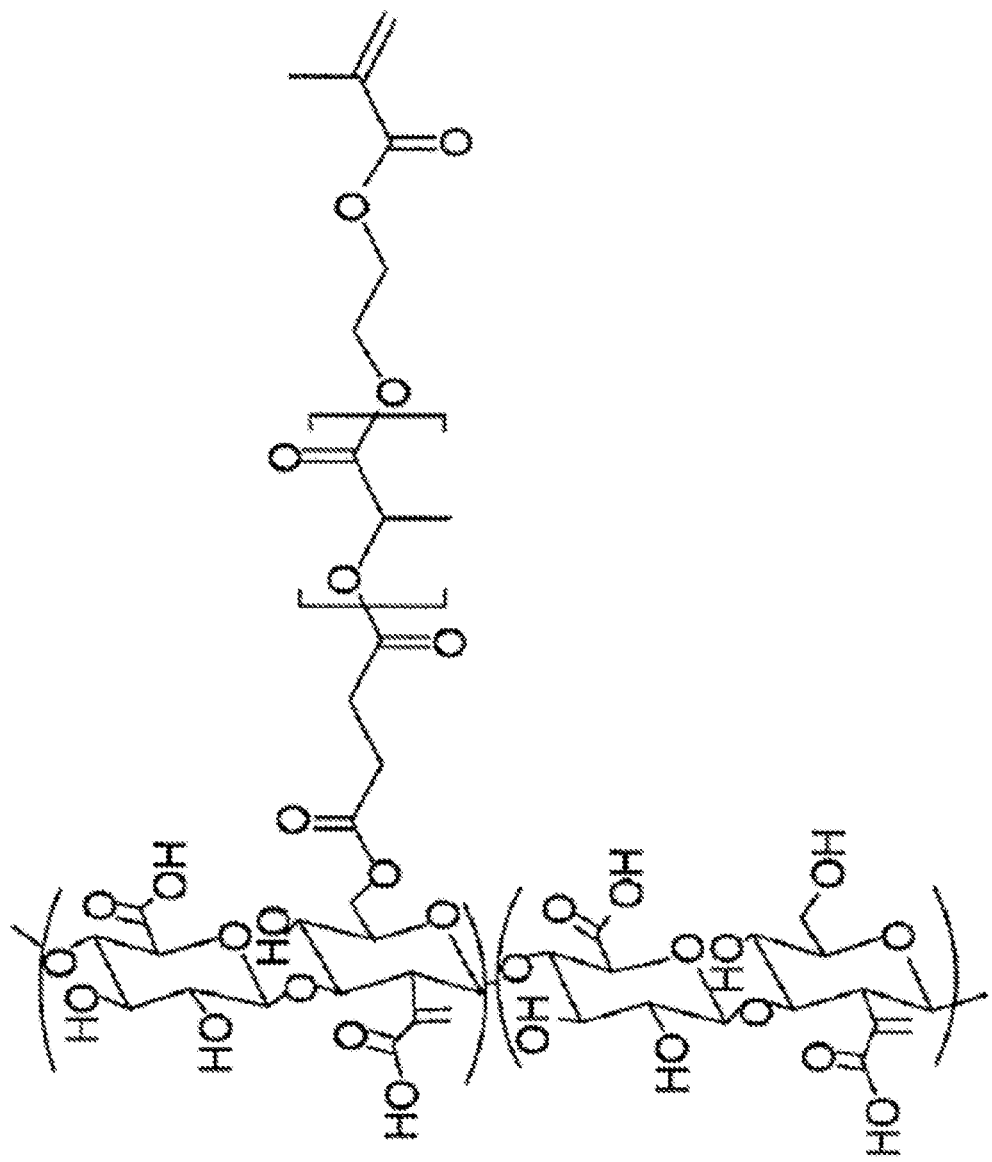
FIGS. 11A-11C depicts the chemical structure of hydrolytically degradable HA macromer (FIG. 11A), degradation with variations in macromer concentration (~1-5%) (FIG. 11B), and representative NMR spectra of the macromer (FIG. 11C)

A major component of the proposed work is utilizing a hydrogel that is comprised of HA and degrades through both hydrolytic and enzymatic mechanisms to better control the temporal properties of the hydrogel structure. Hydrogels satisfying these criteria and the chemical structure and NMR of the macromer is shown in FIG. 11. The HA macromer was similar to those described earlier, but repeat units of lactic acid were placed between the HA backbone and photoreactive methacrylate group. This leads to degradation that can occur enzymatically through the HA backbone, as well as hydrolytically through the lactic acid ester groups. Alterations in the macromer concentration, number of degradable units (x), number of modified hydroxyl groups (n), and type of degradable unit (caprolactone instead of lactic acid) can influence hydrogel degradation. These are readily modified during synthesis.

Figure 11B:
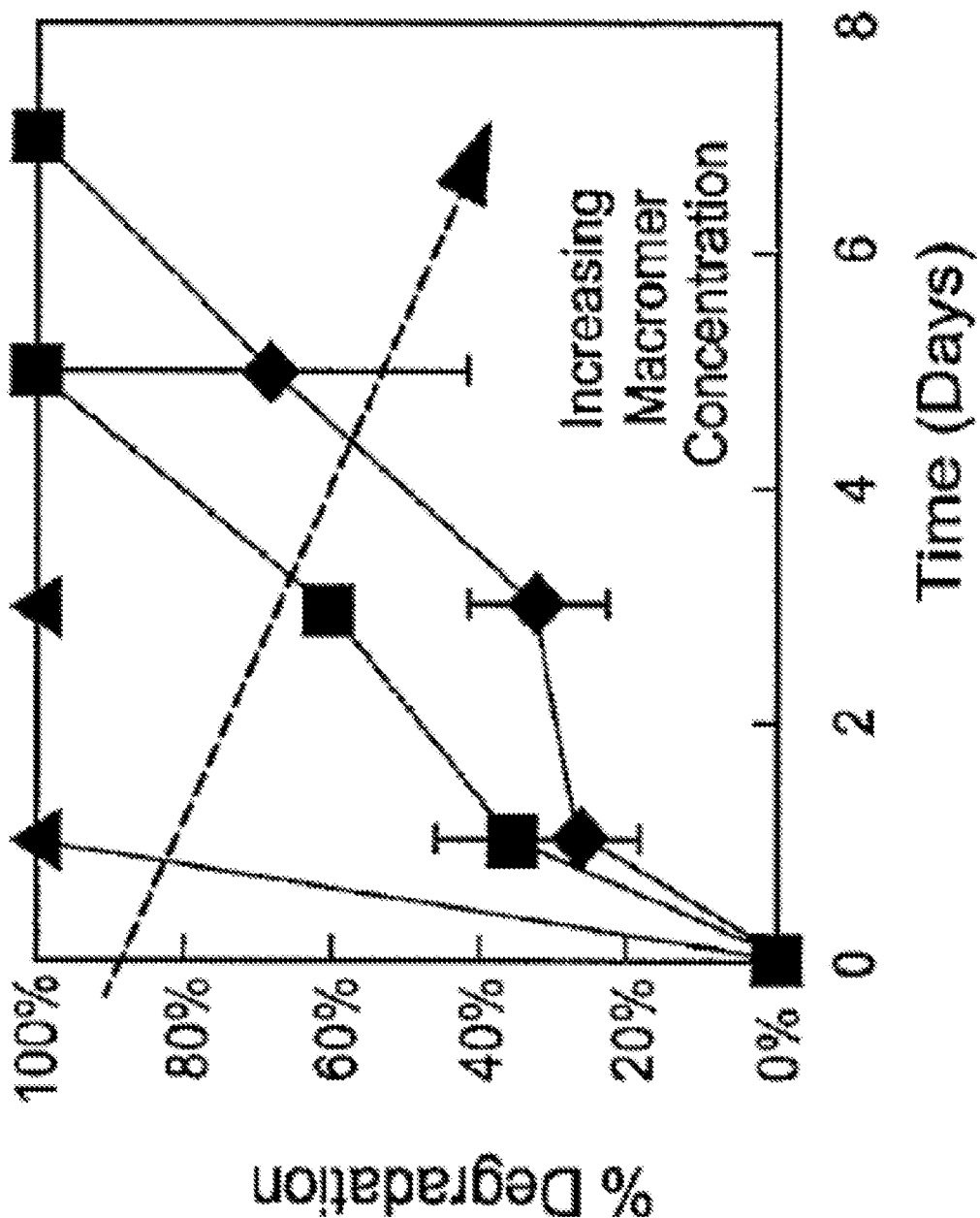
Figure 11C:
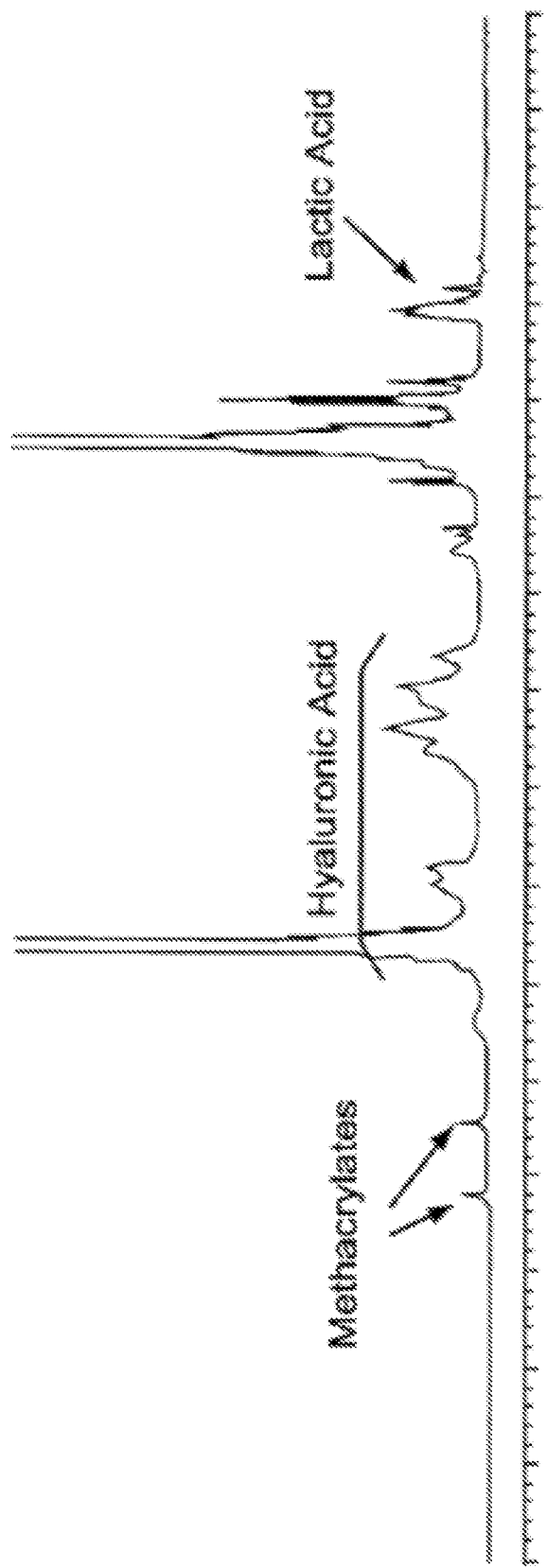
Figure 12A:
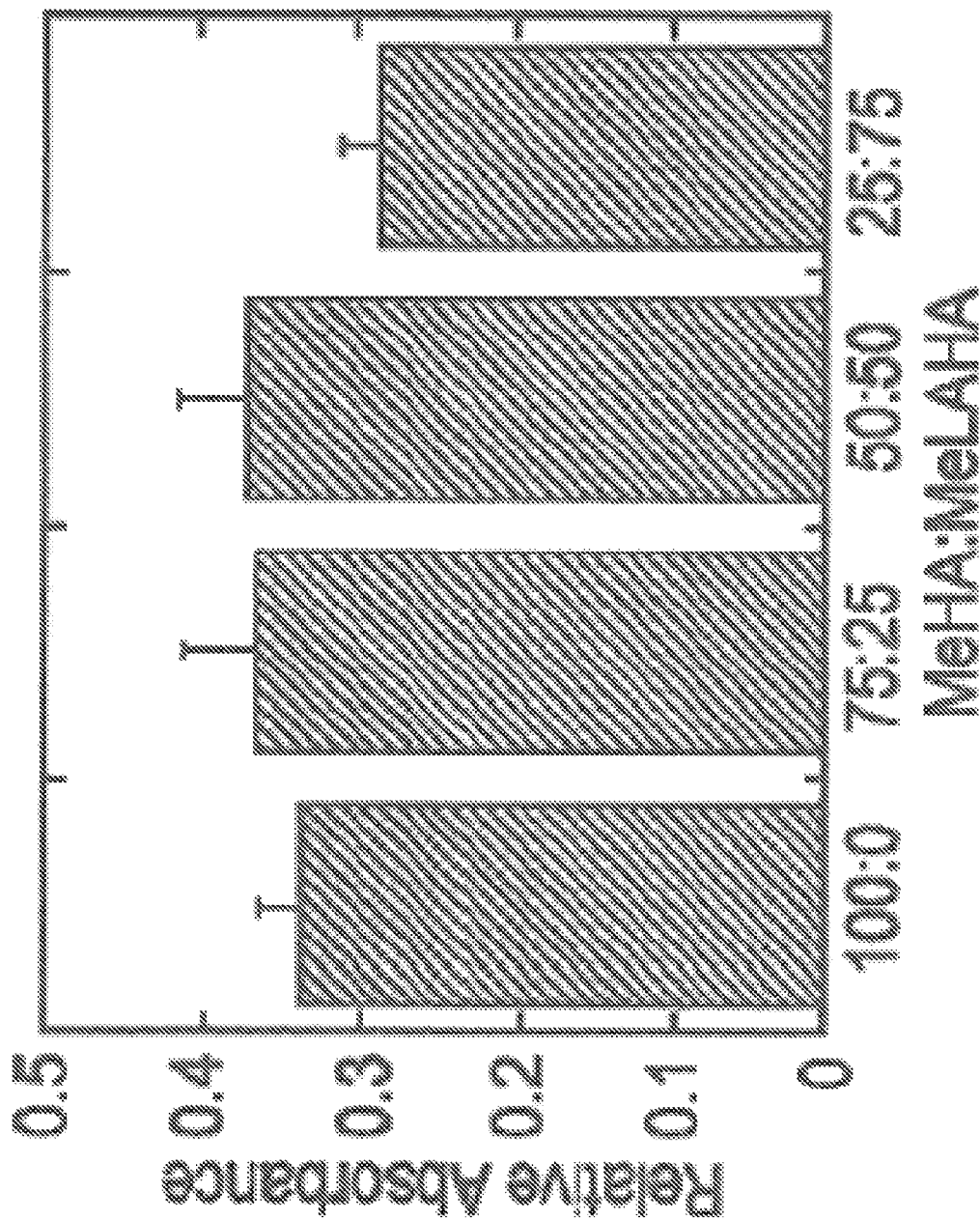
FIGS. 12A-12C depicts MSC viability and interactions with copolymer HA hydrogels, showing mitochondrial activity after 7 days (FIG. 12A), Live/Dead after 6 hrs and 3 days (FIG. 12B), and CS after 14 days of MSCs encapsulated in copolymer HA hydrogels (MeHA:MeLAHA 100:0, 75:25, 50:50, 25:75) (scale bar=200 um for (FIG. 12B) and 100 um for (FIG. 12C))
Figure 12B:
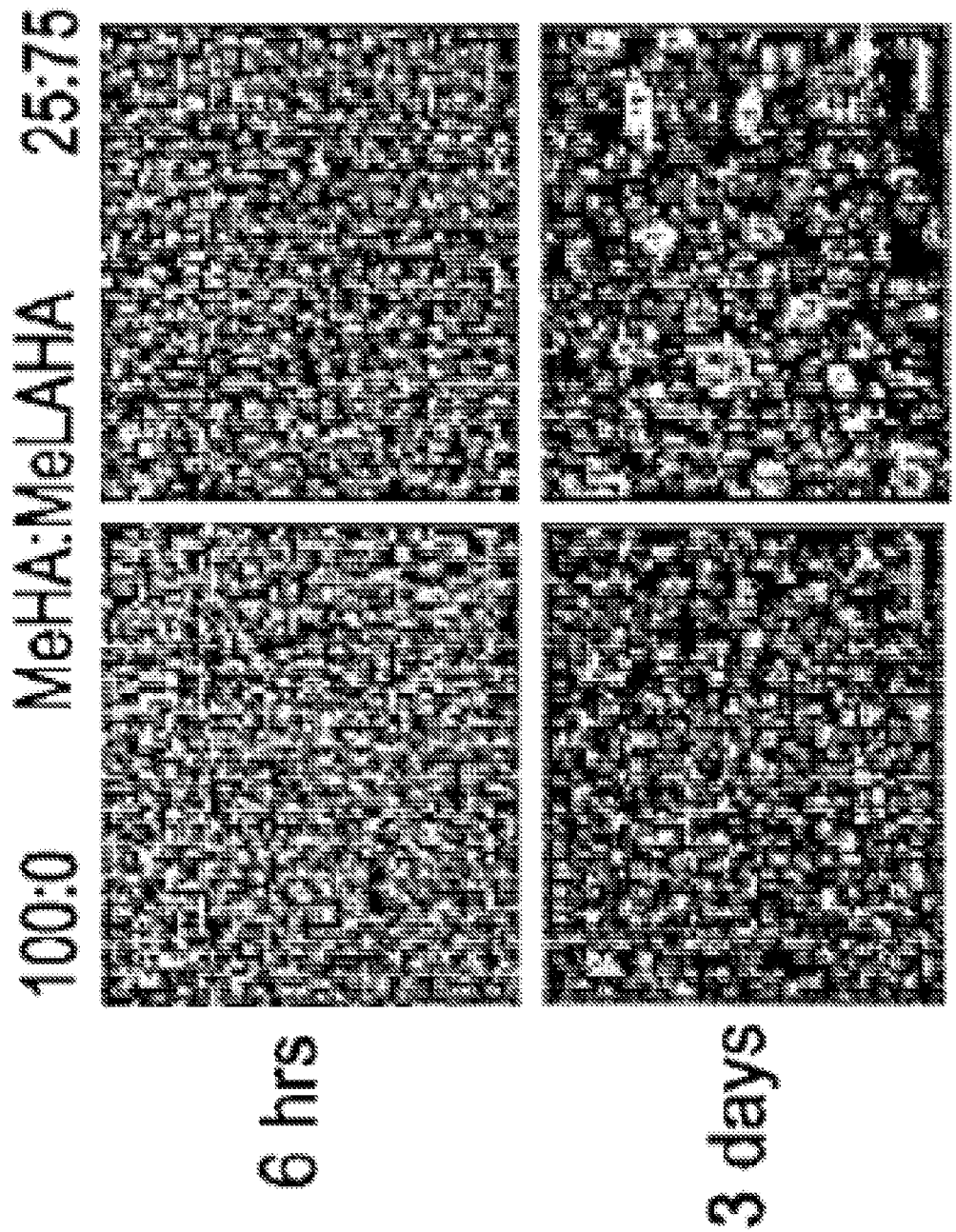
Figure 12C:
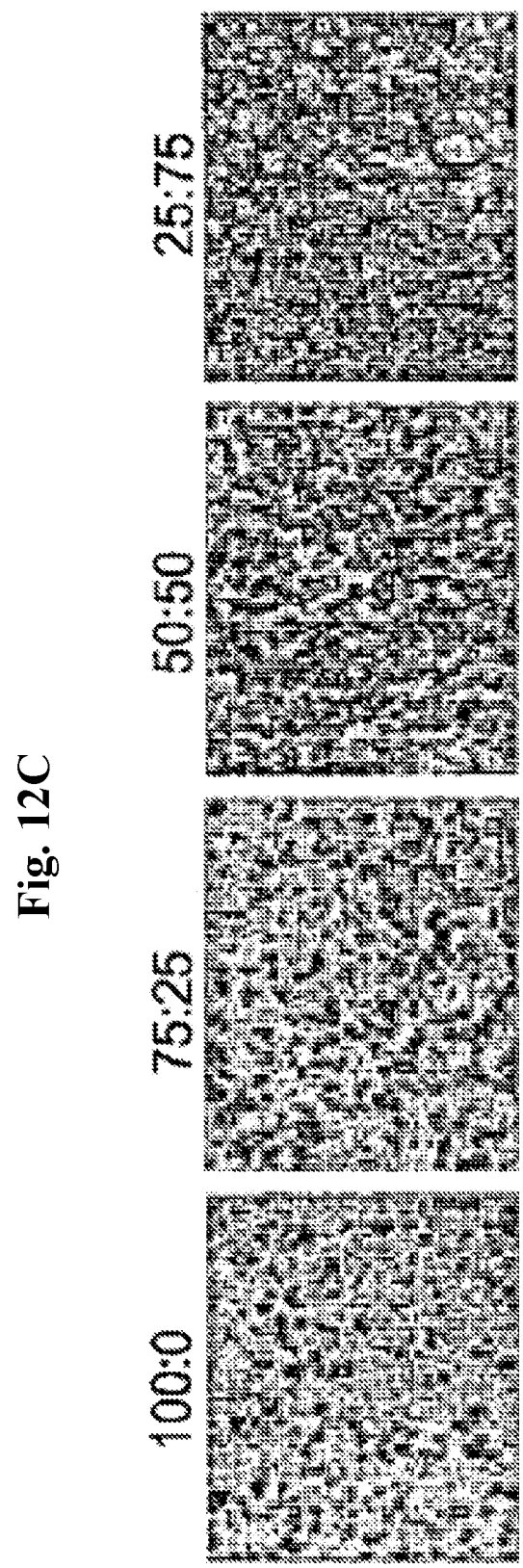
Figure 13:
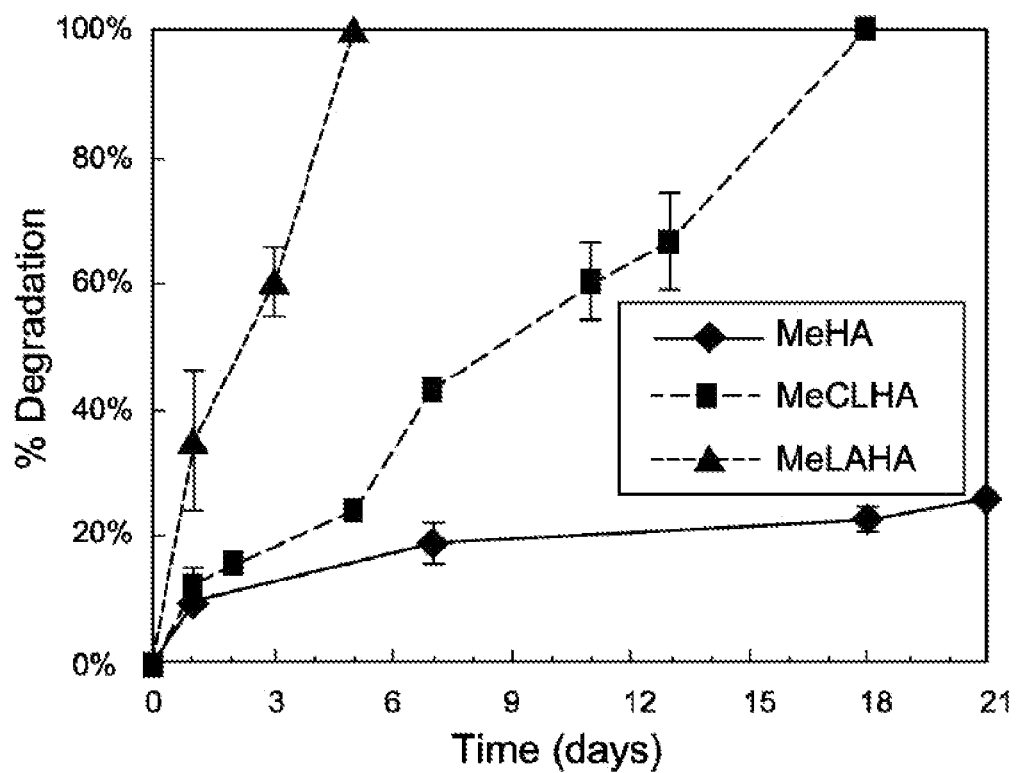
FIG. 13 depicts mass loss profiles of MeCLHA, MeLAHA, and MeHA gels in saline, indicating diversity based on macromer chemistry.

One example of the degradation (measured through release of uronic acid) of these hydrogels with variations in macromer concentration is shown in FIG. 11B. As the concentration is decreased, the hydrogel degrades more quickly, even without HYAL present. Purely enzymatically degradable gels have negligible mass loss under these conditions. The synthesized hydrolytically degraded macromer (MeLAHA) was copolymerized with the previously used enzymatically degradable MeHA (molecular weight–64 kDa, modification–35%) at various ratios (100:0, 75:25, 50:50, 25:75, 0:100 MeHA: MeLAHA) and a concentration of ~2 wt %. Importantly, MSCs remained viable (>95%) after encapsulation in all gels, as evident by the mitochondrial activity and Live/Dead staining (FIG. 12). The cellular morphology changed depending on the copolymer concentrations, with the greater amount of hydrolytically degradable macromer leading to more cell clustering (FIG. 12B). Greater chondroitin sulfate (CS) distribution was observed with increasing inclusion of the MeLAHA (FIG. 12C). Specifically, a gradient of CS (an important ECM molecule in cartilage) distribution corresponded with the amount of MeLAHA. This supports the hypothesis that uniform tissues can be produced more rapidly by altering degradation profiles. Also synthesized was a version of this hydrogel containing caprolactone as the hydrolytically degradable group (MeCLHA). Caprolactone is more hydrolytically stable than lactic acid, so it was thought that hydrogels would degrade slower when formed. HA hydrogels fabricated from the MeCLHA degraded in ~18 days (FIG. 13). The diversity in degradation between the MeLAHA, MeCLHA, and MeHA gels allows for a range of degradation profiles that will be essential for the proposed work.

Example 4

Optimization of tissue formation contributes to the success of a tissue-engineered scaffold. Crosslinking density affects encapsulated cell viability, initial mechanical properties, and the diffusion of nutrients and waste. Degradation affects scaffold properties, cell-scaffold interactions, and the quantity and distribution of extracellular matrix (ECM) from entrapped cells with time. The effects of temporal network structure on scaffold properties and enhanced neocartilage formation were investigated.

Materials and Methods

Figure 8:
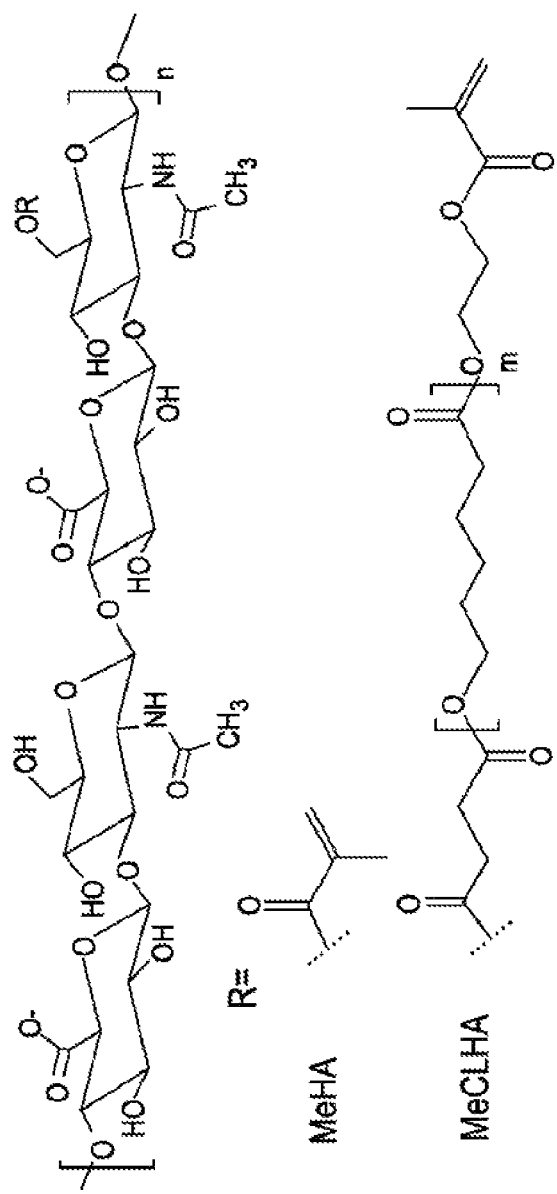
FIG. 8 depicts chemical structures of MeHA and MeCLHA.
Figure 9A:
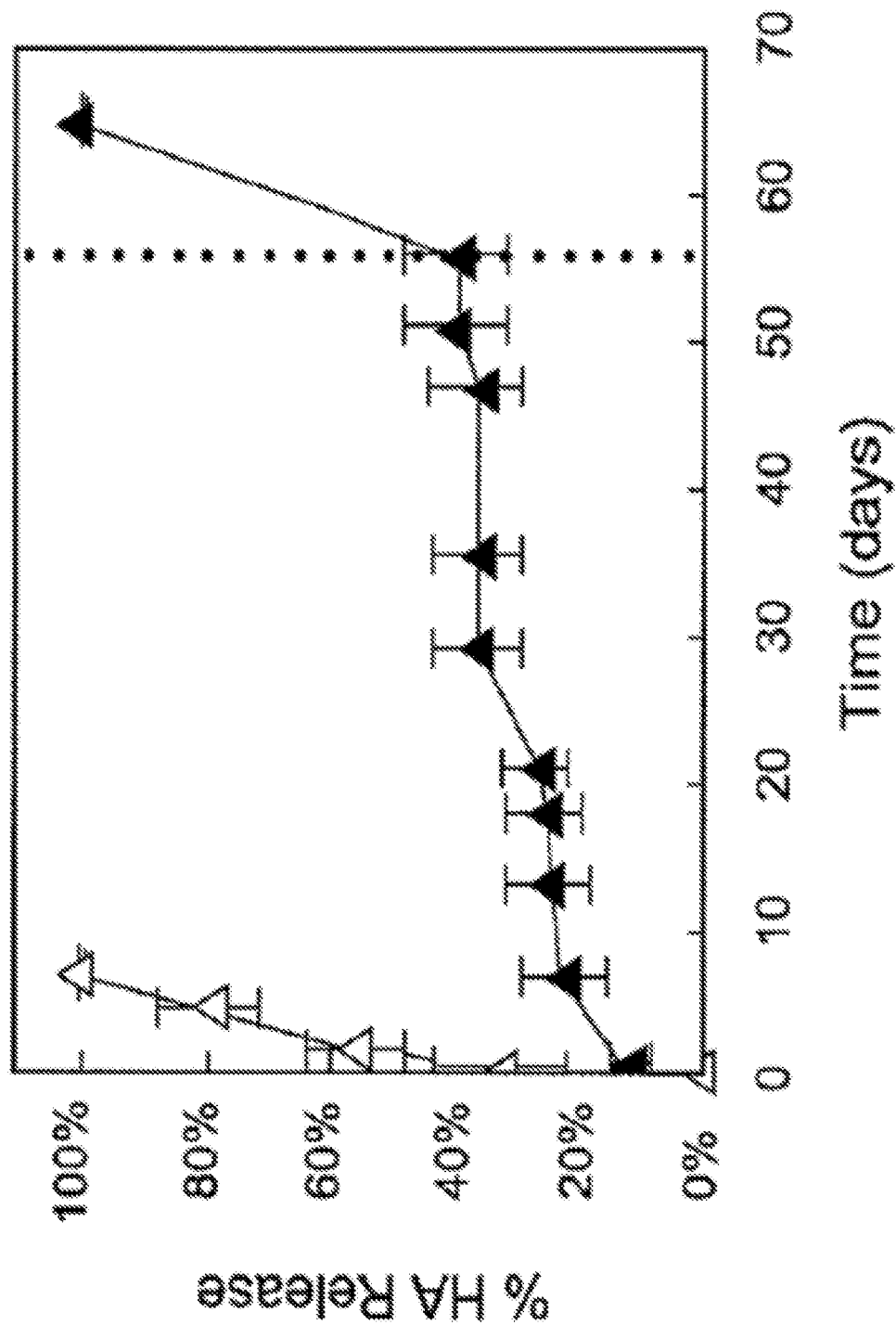
FIGS. 9A-9B depicts (FIG. 9A) Degradation of acellular 2 wt % MeHA (black) and 2 wt % MeCLHA (white).
Figure 9B:
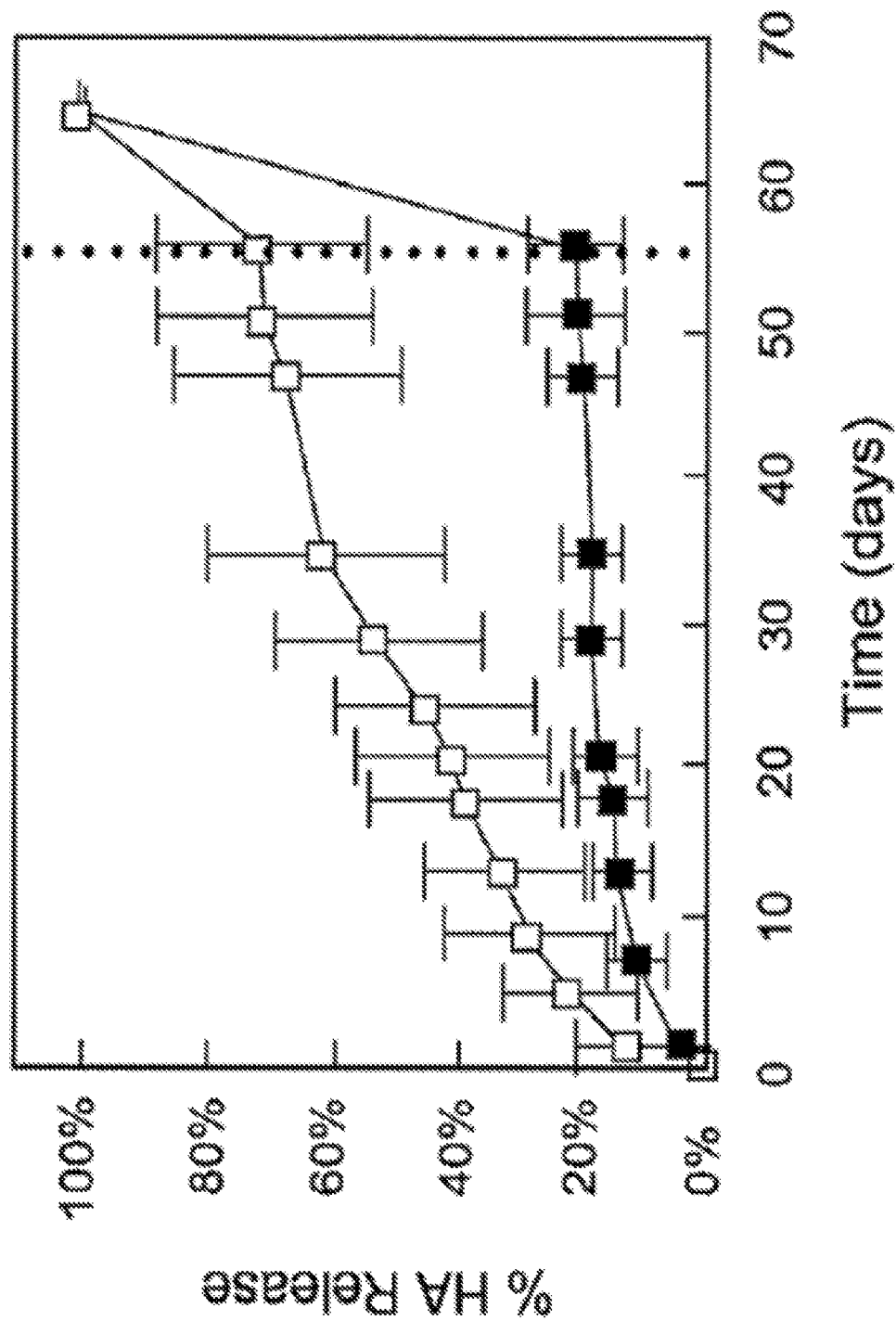

The syntheses of methacrylated HA (MeHA) and methacrylated caprolactone HA (MeCLHA) (FIG. 8) and acellular characterization (e.g., mechanics, degradation) methods were previously reported. Human MSCs (Lonza) were photoencapsulated (20 million cells/mL) in hydrogels of varying macromer concentration (e.g., 5, 2, and 1 wt %) and type (e.g., MeHA, MeCLHA). Hydrogels consisting of 5:0, 4:1, 3:2, 2:3, 2:0, 1.5:0.5, 1:1, and 1:0 MeHA wt %:

MeCLHA wt % were cultured in chondrogenic media supplemented with 10 ng/ml of TGF-b3 for up to 8 weeks in vitro. At various time points, samples (n=5) were measured, mechanically tested in unconfined compression, and digested to determine biochemical content (e.g., DNA, GAG,collagen). Additionally, histological sections were stained for type I and II collagen and chondroitin sulfate to visualize ECM distribution. ANOVA with Tukey's post-hoc test was used to determine significant differences (p<0.05).

Results

Figure 10:
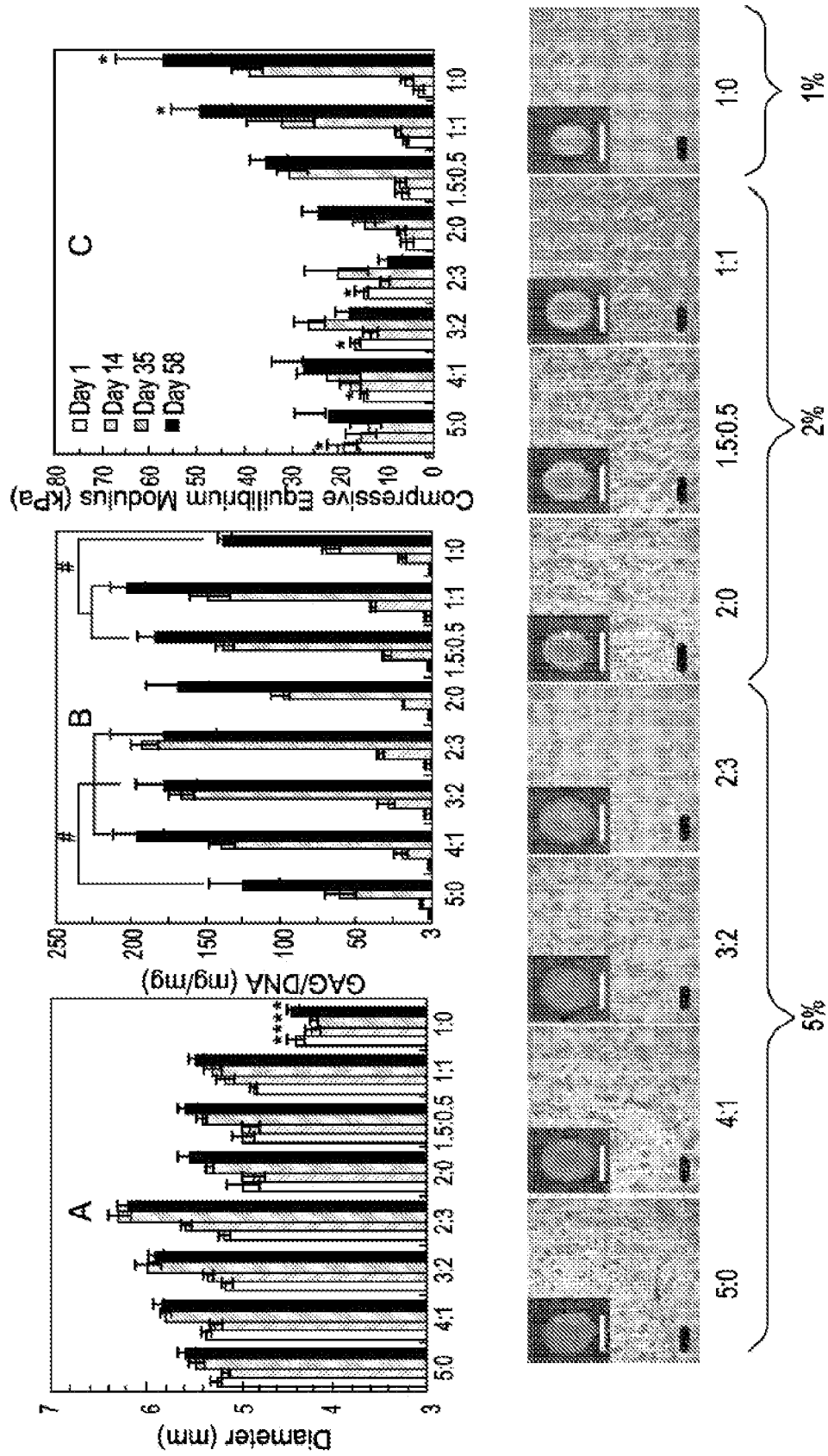
FIGS. 10A-10C depicts Hydrogel diameter (FIG. 10A), GAG/DNA content (FIG. 10B), and compressive equilibrium modulus (FIG. 10C) for 1 (white), 14 (gray), 35 (dark gray), and 56 days (black) of culture. (Bottom) Immunohistochemical staining for chondroitin sulfate after 2 weeks of culture (scale bar=100 mm)—inset: Macroscopic appearance after 8 weeks of culture (scale bar=5 mm)—statistical analysis: * denotes significant difference between starred groups and all other groups for the specified time point and # denotes significant difference between bracketed groups.

Network structures and properties in slowly degrading (enzymatically) HA gequilibrium moduli (1 wt %: 3±1 kPa, 2 wt %: 6±0.5 kPa, 5 wt %: 16±2 kPa) increase with increasing wt % (FIG. 10). However, over time, degradation results in altered scaffold properties, with significant increases in hydrogel diameters for all groups.els have been shown to influence neocartilage formation by chondrocytes3. Specifically, crosslinking density dictates the diffusion of nutrients and waste, and importantly, newly synthesized ECM proteins that contribute to the construct's mechanical properties. However, ECM distribution is often limited without adequate space for diffusion; thus, techniques to better control network evolution with time may improve overall tissue. In this example, hydrolytically degradable repeat units of caprolactone between the HA backbone and methacrylate groups were introduced to allow for controlled hydrogel degradation (FIG. 11).

In addition, in copolymer (MeHA and MeCLHA) hydrogels, degradation rate and temporal mesh size influence tissue formation. Of hydrogels with an initial concentration of 5 wt %, the 4:1 composition exhibits the highest modulus (27±7 kPa) after 8 weeks, where moduli then decrease with increased MeCLHA wt %. Here, larger void spaces created as the hydrogel degrades may allow for the loss of GAGs into the culture medium. However, 2 wt % copolymer hydrogels exhibit increased distributions of chondroitin sulfate after 2 weeks (FIG. 10) with increased MeCLHA content, where the increased ECM distribution was also reflected by increases in both the compressive equilibrium modulus (from 24.1±3.7 to 49.1±6.6 kPa) and the GAG/DNA content (from 169±21 to 201±12 mg GAG/mg DNA) after 8 weeks of culture.

It was observed that a gel that starts at a higher wt % and decreases to a lower wt % is not equivalent to a gel that starts at the lower wt %. Specifically, the 2:3 hydrogels had a significantly greater diameter and lower equilibrium modulus when compared to the 2:0 hydrogels. Also, despite an insignificantly lower equilibrium modulus, the 1:1 hydrogels boast a significantly higher GAG/DNA content (FIG. 3) at 8 weeks. All 2 and 1 wt % hydrogels exhibit significantly increasing moduli and GAG/DNA content over time, reflecting improved tissue quality. Total DNA content was similar in all groups (data not shown).

SUMMARY

These results indicate that tuning scaffold degradation can be used to control neocartilage production and/or distribution by MSCs in HA hydrogels. The faster degrading MeCLHA component of the hydrogel creates void spaces, allowing for the deposition and enhanced distribution of newly synthesized ECM proteins, while the MeHA component provides structural support, maintaining the size and shape of the scaffold. It is also important to note that larger voids created during degradation may result in the reduced retention of ECM proteins. Thus, a careful balance of slow and fast degrading components is needed for optimal growth. Here, the 1:1 hydrogels, with increased mechanical properties and biochemical content over time while retaining scaffold size, show great potential as a scaffold to support the production of functional cartilage tissue by MSCs.

Total macromer wt % affects crosslinking density and can dictate initial hydrogel properties, where initial sample diameters (1 wt %: 4.4±0.1 mm, 2 wt %: 4.9±0.1 mm, 5 wt %: 5.2±0.1 mm) and compressive Example 5

Statement of Purpose

Exogenously delivered bone marrow derived stem cells (BMSCs) have been explored to treat myocardial infarction (MI). While there is evidence that delivering these cells provides some functional benefit to the injured heart, transplanted cell retention and survival in the post-MI environment is extremely low.

As an alternative to cell delivery, the claimed compositions were used in an in situ forming biomaterial system to localize and sustain the release of a chemoattracting cytokine, stromal-derived factor-1 alpha (SDF-1α), to recruit endogenous BMSCs.

SDF-1α is critical to the retention of BMSCs in the bone marrow, but can also induce directional chemotaxis of BMSCs to injured tissues. In the disclosed system, the crosslink density of a hyaluronic acid (HA) hydrogel controls the diffusion of SDF-1α with changes in macromer concentration and extent of reactive group modification. In addition, the hydrogel delivery system is formed in situ to promote integration with the myocardium via a visible light initiated photopolymerization, and is degraded into potentially angiogenic molecules.

Methods 74 kDa HA (Lifecore) was modified with a hydroxyethyl methacrylate (HEMA) group to incorporate photoreactivity and by drolytic degradation. Briefly, HEMA was reacted with succinic anhydride via a ring opening polymerization in the presence of N-methylimidazole to obtain HEMA-COOH, which was then coupled to a tetrabutylammonium (TBA) salt of HA in the presence of 4-Dimethylaminopyridine.

By varying the ratio of HEMA-COOH to HA-TBA, the number of HA units modified with a HEMA group can be controlled. HEMA-HA hydrogels were polymerized with a cytocompatible visible light (VL)—initiated system consisting of 0.02 wt % eosin Y, 225 mM triethanolamine, 37 mM vinylpyrrolidone and a commercially available dental curing lamp. For release kinetics, recombinant human SDF-1α was encapsulated into HEMA-HA hydrogels with two different crosslink densities (n=3 per group) during photopolymerization and released into a buffer over two weeks. Released SDF-1α was quantified using ELISA and reported as percent cumulative release. The ability of the released SDF-1α to chemoattract BMSCs was quantified with a Boyden chamber assay. The number of migrated human mesenchymal stem cells (hMSCs) after 16 hr incubation in response to serial dilutions of SDF-1α released during the first 24 hrs was reported as a fold increase compared to 0 ng/ml SDF-1α.

Result/Discussion

Figure 14A:
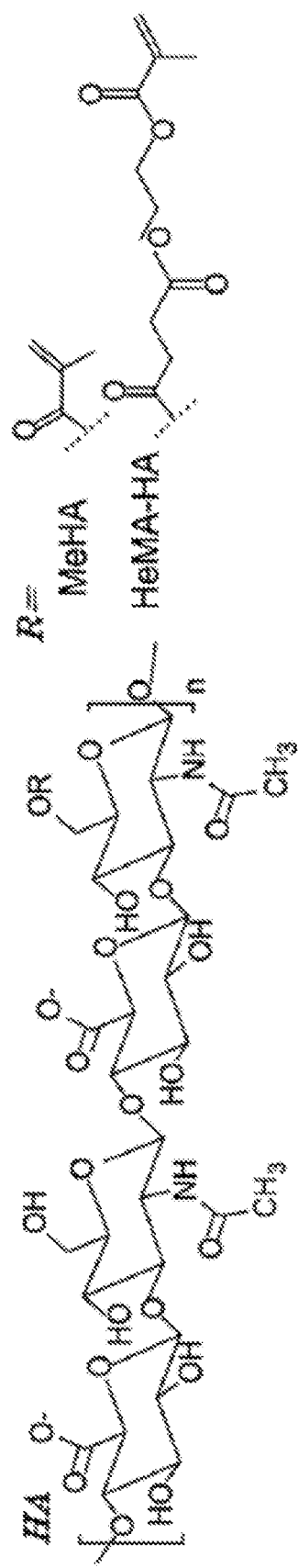
FIGS. 14A-14C illustrates (FIG. 14A) the chemical structures of HeMA-HA and MeHA, (FIG. 14B) degradation time and compressive modulus for 4 different modifications of 4 wt % gels of HeMA-HA, and (FIG. 14C) normalized compressive modulus data of copolymers with degradation—all results used 4 wt % gels and 5 mM APS and TEMED.
Figure 14B:
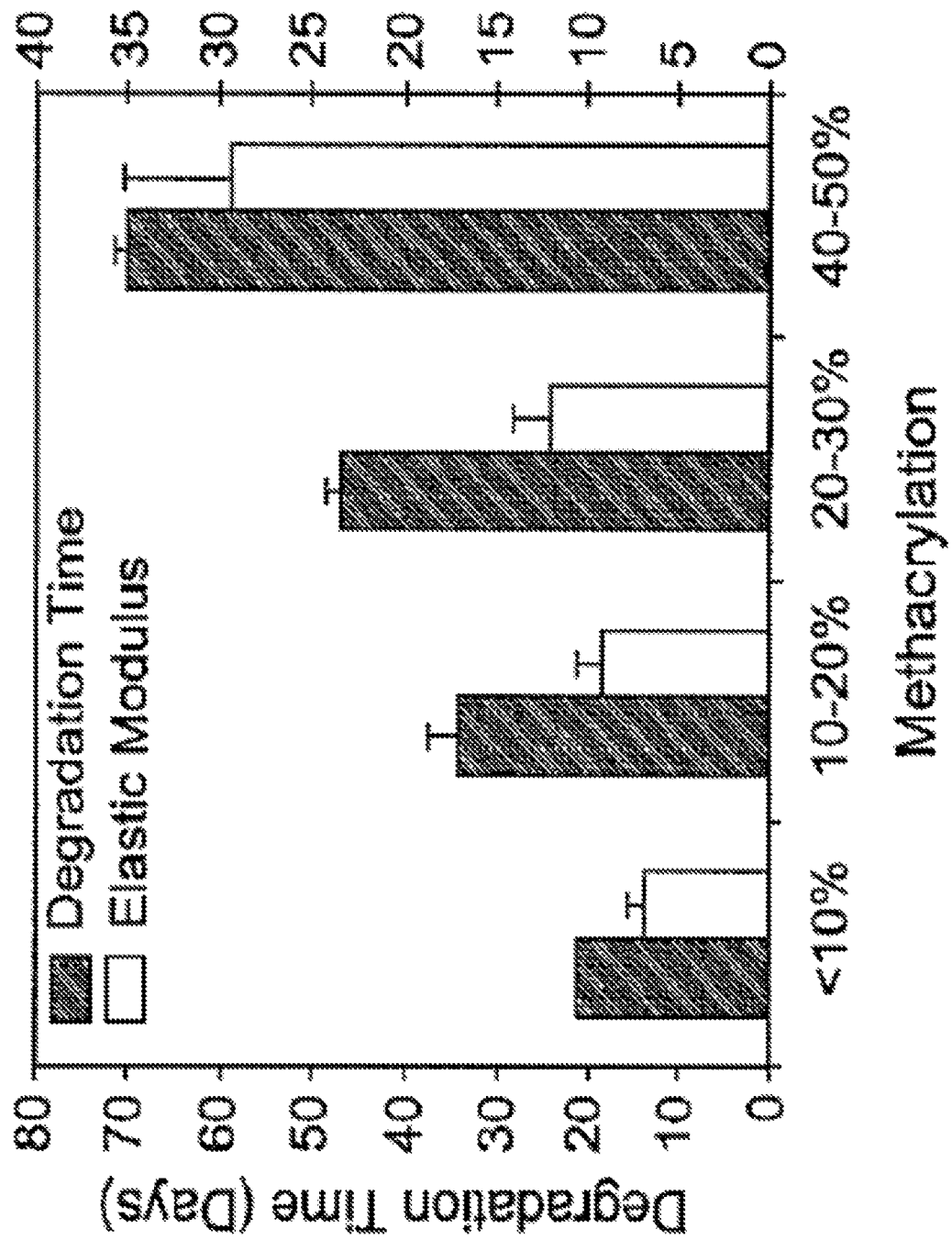
Figure 14C:
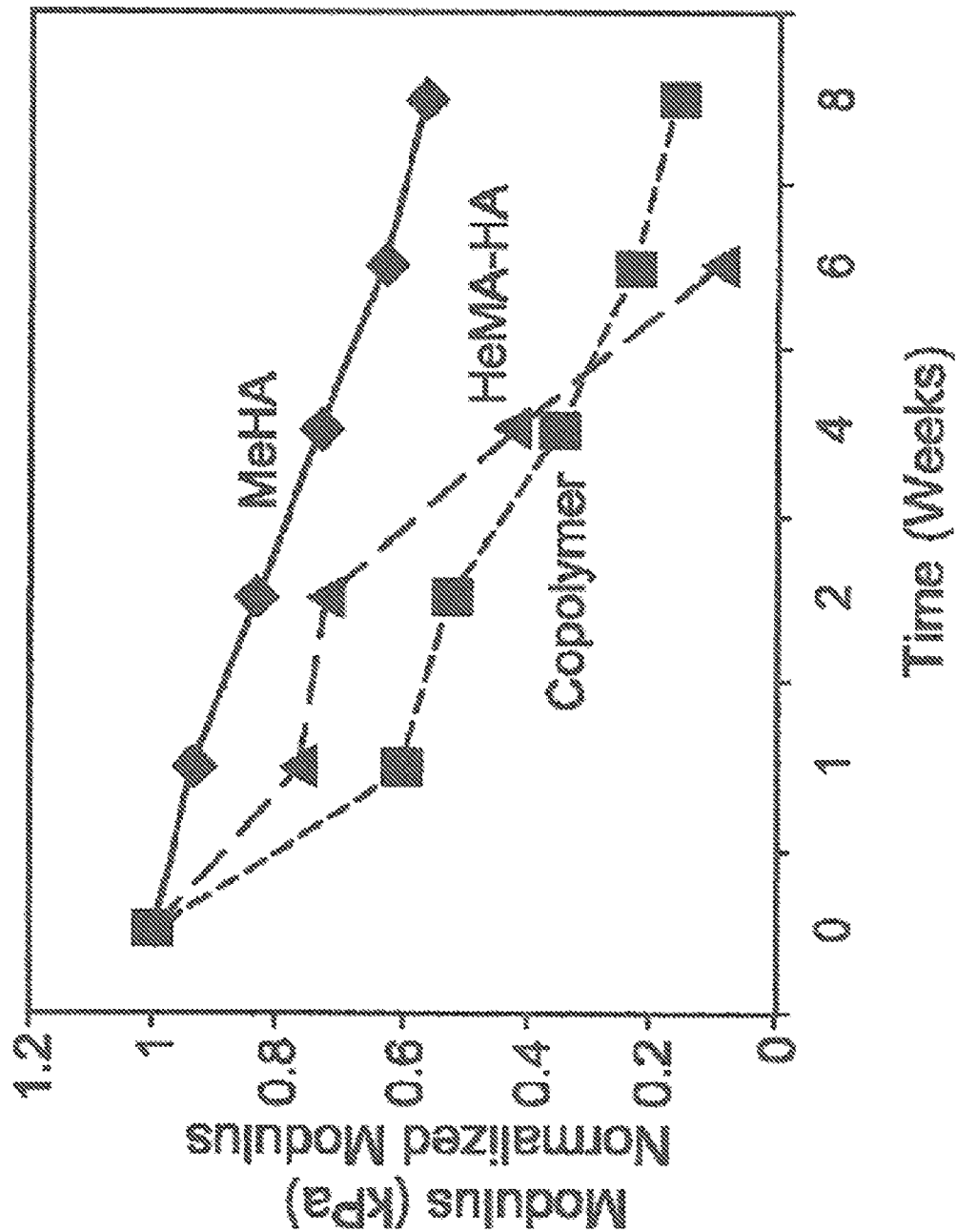

Varying the concentration of HeMA-COOH and $BOC_2O$ allowed for changes in HeMA-HA modification. Without being bound to any one theory, in general, as the degree of methacrylation increased, moduli and degradation rates both increased (FIG. 14). These properties were also adjusted by forming copolymers with the non-hydrolytically degradable MeHA. HeMA-HA (20% modification) and MeHA (100% modification) were used to form homopolymers or a 75:25 copolymer. Compared to MeHA alone, the compressive modulus of the two HeMA-HA gels significantly decreases with time. Thus, such gels are tunable with respect to degradation and moduli.

Figure 15:
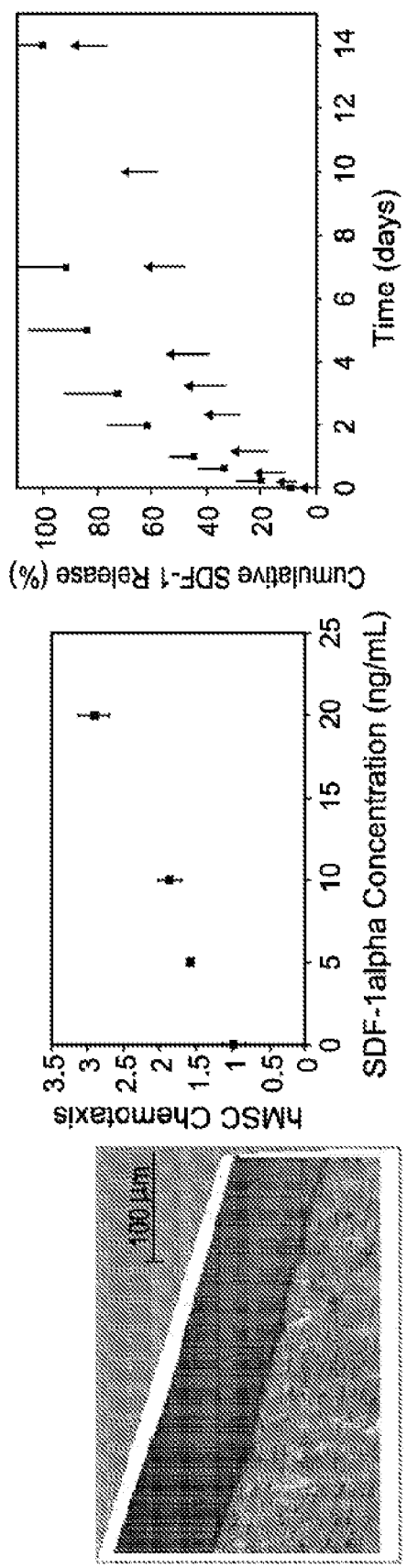
FIG. 15 illustrates H&E (hematoxylin and eosin stain) histology of adherent HEMA-HA hydrogel on murine myocardium (left), activity of released SDF-1α (middle), and release kinetics from 3 wt %, 7% modified (squares) and 6 wt %, 20% modified (triangles) (right)

Hydrogels photopolymerized on murine hearts adhered to the tissue (FIG. 15). In addition, the VL photocrosslinking of the HA hydrogels was rapid, reaching maximal crosslinking within minutes (rheometry data not shown). This photopolymerization system allows us to localize the therapy to the infarct zone in situ without further damaging the vasculature with multiple injections. To direct SDF-1a diffusion into the tissue, a PEG hydrogel with a much higher crosslink density was photopolymerized atop of the HEMA-HA hydrogel. HEMA-HA hydrogels showed a minimal burst release of SDF-1α despite the molecule's small size (~8 kDa). Release was sustained for two weeks from both hydrogel formulations, while the release kinetics were controlled by varying macromer concentration and percent modification of the HA macromer (FIG. 15).

Controlling SDF-1α release kinetics is important to sustain an optimal gradient of the chemoattractant from the myocardium to the bone marrow (through the circulation) to recruit and engraft BMSCs in the injured heart. To this end, the in vitro Boyden migration assay confirmed the activity of released SDF-1α (FIG. 15). hMSCs were recruited in a dose dependent manner towards higher concentrations of released SDF-1α.

Conclusions

The claimed photopolymerizable biomaterial system represents a useful vehicle to sustain the delivery of SDF-1α to the injured myocardium. In addition to ultimately providing a therapeutic benefit post-MI, this system represents a useful platform to study the recruitment of BMSCs through the circulation to injured tissues in vivo.

What is claimed:

1. A composition, comprising:
a polymer comprising a plurality of repeat units,
at least one repeat unit comprising
a biocompatible backbone comprising units of hyaluronic acid; and
a hydrolytically degradable linker disposed between the biocompatible backbone and a crosslinker group, wherein the hydrolytically degradable linker comprises one or more of units of lactic acid, caprolactone, glycolic acid, an anhydride, or an orthoester,
the crosslinker group covalently binding at least one repeat unit to a second repeat unit comprising methacrylate monomers;
wherein said repeat units are covalently bonded to one another, and
wherein the hydrolytically degradable linker degrades upon exposure to an aqueous medium.

2. The composition of claim 1, further comprising a cell.

3. The composition of claim 2, wherein the cell comprises a mammalian cell.

4. The composition of claim 2, wherein the cell comprises a stem cell.

5. A method of synthesizing a macromer according to claim 1, comprising:
reacting a first compound comprising methacrylate with a compound comprising lactide to give rise to a second compound comprising a methacrylic group, a lactic acid, and an OH end group;
converting the —OH end group to a carboxylic acid end group;
reacting the carboxylic acid end group to give rise to a functionalized end group; and
reacting the functionalized end group with a salt of an acidic polysaccharide, so as to give rise to a macromer comprising a polymerizing moiety and a hydrolytically degradable linker, wherein the hydrolytically degradable linker degrades upon exposure to an aqueous medium.

6. The method of claim 5, wherein the converting the —OH end group to a carboxylic acid group comprises reaction with succinic anhydride in the presence of pyridine and dimethylaminopropylpyridine.

7. The method of claim 5, wherein reacting the carboxylic acid group comprises reacting N-hydroxysuccinimide and dicyclyhexylcarbodiimide.

8. The method of claim 5, wherein the salt of the acidic polysaccharide comprises tetrabutyl amine.

9. A method of controllably delivering an agent, comprising:
disposing a quantity of an agent within a polymeric composition according to claim 1 comprising a plurality of first repeat units,
at least one first repeat unit comprising
a biocompatible backbone comprising units of hyaluronic acid monomers; and
a hydrolytically degradable linker bound to the biocompatible repeat unit, to the polymerizing moiety, or to both,
wherein the hydrolytically degradable linker degrades upon exposure to an aqueous medium;
exposing the delivery composition to an aqueous medium so as to hydrolyze the hydrolytically degradable linker such at least a portion of the quantity of the agent is released from the polymeric composition
wherein said polymeric composition comprising a polymer comprising at least one of
(i) at least one repeat unit that comprises hyaluronic acid and a methacrylate, at least one lactic acid being disposed between the hyaluronic acid and the methacrylate, or
(ii) at least one repeat unit that comprises hyaluronic acid and a methacrylate, at least one caprolactone being disposed between the hyaluronic acid and the methacrylate.

10. The method of claim 9, further comprising contacting the delivery composition to a tissue of a subject.

11. The method of claim 10, further comprising disposing a capping material along at least a portion of the delivery composition such that release of the agent is preferentially directed into the tissue.

12. The method of claim 11, wherein the capping material has a density greater than that of the delivery composition.

13. The method of claim 9, wherein the agent comprises a stem cell, a cytokine, a chemotherapeutic, or any combination thereof.

14. A composition of claim 1, consisting essentially of:
a polymer comprising a plurality of repeat units,
at least one repeat unit comprising
a biocompatible backbone comprising units of hyaluronic acid; and
a hydrolytically degradable linker disposed between the biocompatible backbone and a crosslinker group, wherein the hydrolytically degradable linker comprises one or more of lactic acid, caprolactone, glycolic acid, and anhydride or an ester, the crosslinker group covalently binding at least one repeat unit to a second repeat unit wherein said composition further comprises, comprising a polymer comprising at least one of
  (i) at least one repeat unit that comprises hyaluronic acid and a methacrylate, at least one lactic acid being disposed between the hyaluronic acid and the methacrylate, or
  (ii) at least one repeat unit that comprises hyaluronic acid and a methacrylate, at least one caprolactone being disposed between the hyaluronic acid and the methacrylate.

15. A composition of claim 1, consisting essentially of:
a polymer comprising a plurality of repeat units,
  at least one repeat unit comprising
    a biocompatible backbone comprising units of hyaluronic acid; and
    a hydrolytically degradable linker disposed between the biocompatible backbone and a crosslinker group, wherein the hydrolytically degradable linker comprises one or more of lactic acid, caprolactone, glycolic acid, and anhydride or an ester, the crosslinker group covalently binding at least one repeat unit to a second repeat unit;
  wherein said composition further comprises a polymer comprising at least one of
    (i) at least one repeat unit that comprises hyaluronic acid and a methacrylate, at least one lactic acid being disposed between the hyaluronic acid and the methacrylate, or
    (ii) at least one repeat unit that comprises hyaluronic acid and a methacrylate, at least one caprolactone being disposed between the hyaluronic acid and the methacrylate; and
  a plurality of cells.

16. The composition of claim 1, wherein the first repeat unit and the second repeat unit are different on the basis of the formulas of their backbones, their polymerizable groups, or on the basis of the hydrolytically degradable linkers, or a combination thereof.

17. The composition of claim 16, wherein the first repeat unit and the second repeat unit differ on the basis of the formulas of their hydrolytically degradable linkers.

* * * * *

UNITED STATES PATENT AND TRADEMARK OFFICE
CERTIFICATE OF CORRECTION

PATENT NO. : 11,090,387 B2  
APPLICATION NO. : 13/139537  
DATED : August 17, 2021  
INVENTOR(S) : Jason Alan Burdick et al.

Page 1 of 1

It is certified that error appears in the above-identified patent and that said Letters Patent is hereby corrected as shown below:

In the Specification

<u>Column 1,</u>  
Lines 16-19, delete "This invention was made with government support under grant numbers DE015761 and DMR0520020 awarded by the National Institutes of Health. The government has certain rights in the invention."

And insert -- This invention was made with government support under Contract No. DE015761 awarded by the National Institutes of Health and Contract No. 0520020 awarded by the National Science Foundation. The government has certain rights in the invention. --.

Signed and Sealed this  
Fifth Day of October, 2021

Drew Hirshfeld  
*Performing the Functions and Duties of the*  
*Under Secretary of Commerce for Intellectual Property and*  
*Director of the United States Patent and Trademark Office*